United States Patent
Levy et al.

(10) Patent No.: US 10,080,486 B2
(45) Date of Patent: Sep. 25, 2018

(54) MULTI-CAMERA ENDOSCOPE HAVING FLUID CHANNELS

(75) Inventors: Avi Levy, Herzliya (IL); Moshe Levi, Ganei Tikva (IL); Golan Salman, Atlit (IL); Yaniv Kirma, Tzrufa (IL)

(73) Assignee: EndoChoice Innovation Center Ltd., Caesarea (IL)

( * ) Notice: Subject to any disclaimer, the term of this patent is extended or adjusted under 35 U.S.C. 154(b) by 329 days.

(21) Appl. No.: 13/822,908

(22) PCT Filed: Sep. 20, 2011

(86) PCT No.: PCT/IL2011/000745
§ 371 (c)(1),
(2), (4) Date: Mar. 13, 2013

(87) PCT Pub. No.: WO2012/038958
PCT Pub. Date: Mar. 29, 2012

(65) Prior Publication Data
US 2013/0172676 A1      Jul. 4, 2013

Related U.S. Application Data

(60) Provisional application No. 61/384,354, filed on Sep. 20, 2010.

(51) Int. Cl.
*A61B 1/00* (2006.01)
*A61B 1/12* (2006.01)
(Continued)

(52) U.S. Cl.
CPC .............. *A61B 1/126* (2013.01); *A61B 1/008* (2013.01); *A61B 1/00091* (2013.01);
(Continued)

(58) Field of Classification Search
CPC ......... A61B 1/05; A61B 1/018; A61B 1/0684; A61B 1/126; A61B 1/00091; A61B 1/053;
(Continued)

(56) References Cited

U.S. PATENT DOCUMENTS 3,639,714 A    2/1972  Fujimoto
3,955,064 A    5/1976  Demetrio
(Continued)

FOREIGN PATENT DOCUMENTS

CN    1376443       10/2002
CN    2829646 Y     10/2006
(Continued)

OTHER PUBLICATIONS

International Search Report of PCT/IL2011/000745, dated May 8, 2012.
(Continued)

*Primary Examiner* — Timothy J Neal
(74) *Attorney, Agent, or Firm* — Bookoff McAndrews, PLLC

(57) ABSTRACT

There is provided a tip section of a multi-camera endoscope, the tip section comprising a unitary fluid channeling component adapted to channel fluid for insufflations and/or irrigation, the unitary fluid channeling component comprising: a proximal opening adapted to receive a fluid tube, the proximal opening being in fluid flow connection with a front fluid (I/I) channel and a side fluid channel.

20 Claims, 29 Drawing Sheets

US 10,080,486 B2

Page 2

(51) Int. Cl.
*A61B 1/015* (2006.01)
*A61B 1/008* (2006.01)
*A61B 1/018* (2006.01)
*A61B 1/05* (2006.01)
*A61B 1/06* (2006.01)
*A61B 1/31* (2006.01)
*A61B 1/04* (2006.01)

(52) U.S. Cl.
CPC ...... *A61B 1/00094* (2013.01); *A61B 1/00096* (2013.01); *A61B 1/00114* (2013.01); *A61B 1/00177* (2013.01); *A61B 1/00181* (2013.01); *A61B 1/015* (2013.01); *A61B 1/018* (2013.01); *A61B 1/053* (2013.01); *A61B 1/0676* (2013.01); *A61B 1/0684* (2013.01); *A61B 1/31* (2013.01)

(58) Field of Classification Search
CPC ... A61B 1/00096; A61B 1/31; A61B 1/00181; A61B 1/0676; A61B 1/008; A61B 1/00094; A61B 1/00114
USPC .............. 600/109, 128, 129, 130; 356/241.3, 356/241.5
See application file for complete search history.

(56) References Cited

U.S. PATENT DOCUMENTS

| | | |
|---|---|---|
| 4,037,588 A | 7/1977 | Heckele |
| 4,084,401 A | 4/1978 | Belardi |
| 4,253,448 A | 3/1981 | Terada |
| 4,261,345 A | 4/1981 | Yamaguchi |
| 4,402,313 A | 9/1983 | Yabe |
| 4,414,608 A | 11/1983 | Furihata |
| 4,439,030 A | 3/1984 | Ueda |
| 4,469,090 A | 9/1984 | Konomura |
| 4,494,549 A | 1/1985 | Namba |
| 4,522,196 A | 6/1985 | Cunningham |
| 4,565,423 A | 1/1986 | Ueda |
| 4,576,144 A | 3/1986 | Ishii |
| 4,588,294 A | 5/1986 | Siegmund |
| 4,590,923 A | 5/1986 | Watanabe |
| 4,641,635 A | 2/1987 | Yabe |
| 4,699,463 A | 10/1987 | D |
| 4,708,126 A | 11/1987 | Toda |
| 4,727,859 A | 3/1988 | Lia |
| 4,736,732 A | 4/1988 | Shimonaka |
| 4,753,222 A | 6/1988 | Morishita |
| 4,764,001 A | 8/1988 | Yokota |
| 4,794,913 A | 1/1989 | Shimonaka |
| 4,801,792 A | 1/1989 | Yamasita |
| 4,841,952 A | 6/1989 | Sato |
| 4,846,154 A | 7/1989 | MacAnally |
| 4,868,644 A | 9/1989 | Yabe |
| 4,877,314 A | 10/1989 | Kanamori |
| 4,878,485 A | 11/1989 | Adair |
| 4,888,639 A | 12/1989 | Yabe |
| 4,902,115 A | 2/1990 | Takahashi |
| 4,905,670 A | 3/1990 | Adair |
| 4,914,521 A | 4/1990 | Adair |
| 4,974,075 A | 11/1990 | Nakajima |
| 4,976,522 A | 12/1990 | Igarashi |
| 4,982,724 A | 1/1991 | Saito |
| 4,984,878 A | 1/1991 | Miyano |
| 4,998,182 A | 3/1991 | Krauter |
| 5,166,787 A | 11/1992 | Irion |
| 5,193,525 A | 3/1993 | Silverstein |
| 5,239,983 A | 8/1993 | Katsurada |
| 5,296,971 A | 3/1994 | Mori |
| 5,299,561 A | 4/1994 | Yoshimoto |
| 5,305,121 A | 4/1994 | Moll |
| 5,309,227 A | 5/1994 | Inoue |
| 5,313,934 A | 5/1994 | Wiita |
| 5,339,800 A | 8/1994 | Wiita |
| 5,359,456 A | 10/1994 | Kikuchi |
| 5,380,049 A | 1/1995 | Smowton |
| 5,386,817 A * | 2/1995 | Jones ................. A61B 1/00091 138/108 |
| 5,398,056 A | 3/1995 | Yabe |
| 5,408,623 A | 4/1995 | Dolidon |
| 5,412,478 A | 5/1995 | Ishihara |
| 5,420,644 A | 5/1995 | Watanabe |
| 5,432,543 A | 7/1995 | Hasegawa |
| 5,436,767 A | 7/1995 | Suzuki |
| 5,447,148 A | 9/1995 | Oneda |
| 5,452,391 A | 9/1995 | Chou |
| 5,460,167 A | 10/1995 | Yabe |
| 5,475,420 A | 12/1995 | Buchin |
| 5,483,951 A | 1/1996 | Frassica |
| 5,485,316 A | 1/1996 | Mori |
| 5,489,256 A | 2/1996 | Adair |
| 5,507,717 A | 4/1996 | Kura |
| 5,512,940 A | 4/1996 | Takasugi |
| 5,515,449 A | 5/1996 | Tsuruoka |
| 5,518,501 A | 5/1996 | Oneda |
| 5,518,502 A * | 5/1996 | Kaplan et al. ................. 600/157 |
| 5,547,455 A | 8/1996 | McKenna |
| 5,547,457 A | 8/1996 | Tsuyuki |
| 5,550,582 A | 8/1996 | Takasugi |
| 5,585,840 A | 12/1996 | Watanabe |
| 5,587,839 A | 12/1996 | Miyano |
| 5,589,874 A | 12/1996 | Buchin |
| 5,592,216 A | 1/1997 | Uehara |
| 5,605,530 A | 2/1997 | Fischell |
| 5,609,560 A | 3/1997 | Ichikawa |
| 5,617,136 A | 4/1997 | Iso |
| 5,630,782 A | 5/1997 | Adair |
| 5,653,677 A | 8/1997 | Okada |
| 5,656,011 A | 8/1997 | Uihlein |
| 5,662,588 A | 9/1997 | Iida |
| 5,675,378 A | 10/1997 | Takasugi |
| 5,679,110 A | 10/1997 | Hamazaki |
| 5,685,823 A * | 11/1997 | Ito et al. ........................ 600/127 |
| 5,701,155 A | 12/1997 | Wood |
| 5,702,345 A | 12/1997 | Wood |
| 5,702,347 A | 12/1997 | Yabe |
| 5,707,344 A | 1/1998 | Nakazawa |
| 5,716,323 A | 2/1998 | Lee |
| 5,725,474 A | 3/1998 | Yasui |
| 5,725,476 A * | 3/1998 | Yasui et al. ................... 600/127 |
| 5,725,477 A | 3/1998 | Yasui |
| 5,728,045 A | 3/1998 | Komi |
| 5,751,340 A | 5/1998 | Strobl |
| 5,764,809 A | 6/1998 | Nomami |
| 5,777,797 A | 7/1998 | Miyano |
| 5,782,751 A | 7/1998 | Matsuno |
| 5,793,539 A | 8/1998 | Konno |
| 5,800,341 A | 9/1998 | McKenna |
| 5,812,187 A | 9/1998 | Watanabe |
| 5,830,124 A | 11/1998 | Suzuki |
| 5,836,894 A | 11/1998 | Sarvazyan |
| 5,852,511 A | 12/1998 | Tateyama |
| 5,860,913 A | 1/1999 | Yamaya |
| 5,870,234 A | 2/1999 | EbbesmeierneeSchitthof |
| 5,871,439 A | 2/1999 | Takahashi |
| 5,871,440 A | 2/1999 | Okada |
| 5,876,326 A | 3/1999 | Takamura |
| 5,879,284 A | 3/1999 | Tsujita |
| 5,894,322 A | 4/1999 | Hamano |
| 5,912,764 A | 6/1999 | Togino |
| 5,913,817 A | 6/1999 | Lee |
| 5,914,810 A | 6/1999 | Watts |
| 5,916,148 A | 6/1999 | Tsuyuki |
| 5,929,901 A | 7/1999 | Adair |
| 5,930,424 A | 7/1999 | Heimberger |
| 5,933,275 A | 8/1999 | Igarashi |
| 5,933,282 A | 8/1999 | Tomioka |
| 5,936,773 A | 8/1999 | Togino |
| 5,940,126 A | 8/1999 | Kimura |
| 5,961,445 A | 10/1999 | Chikama |
| 5,969,888 A | 10/1999 | Sukekawa |
| 5,986,693 A | 11/1999 | Adair |
| 5,989,185 A | 11/1999 | Miyazaki |

(56) References Cited

U.S. PATENT DOCUMENTS

| | | |
|---|---|---|
| 5,993,037 A | 11/1999 | Tomioka |
| 5,995,136 A | 11/1999 | Hattori |
| 6,009,189 A | 12/1999 | Schaack |
| 6,025,873 A | 2/2000 | Nishioka |
| 6,043,839 A | 3/2000 | Adair |
| 6,069,698 A | 5/2000 | Ozawa |
| 6,080,104 A | 6/2000 | Ozawa |
| 6,104,540 A | 8/2000 | Hayakawa |
| 6,110,127 A | 8/2000 | Suzuki |
| 6,117,068 A | 9/2000 | Gourley |
| 6,124,989 A | 9/2000 | Oode |
| 6,139,175 A | 10/2000 | Tomioka |
| 6,139,490 A | 10/2000 | Breidenthal |
| 6,147,808 A | 11/2000 | Togino |
| 6,163,401 A | 12/2000 | Igarashi |
| 6,166,858 A | 12/2000 | Togino |
| 6,181,481 B1 | 1/2001 | Yamamoto |
| 6,184,923 B1 | 2/2001 | Miyazaki |
| 6,185,046 B1 | 2/2001 | Togino |
| 6,196,967 B1 | 3/2001 | Lim |
| 6,201,646 B1 | 3/2001 | Togino |
| 6,201,648 B1 | 3/2001 | Togino |
| 6,210,322 B1 | 4/2001 | Byrne |
| 6,211,904 B1 | 4/2001 | Adair |
| 6,215,517 B1 | 4/2001 | Takahashi |
| 6,217,500 B1 | 4/2001 | Helseth |
| 6,245,086 B1 | 6/2001 | Storz |
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,375,610 B2 | 4/2002 | Verschuur |
| 6,387,045 B1 | 5/2002 | Takahashi |
| 6,398,723 B1 | 6/2002 | Kehr |
| 6,400,514 B2 | 6/2002 | Minami |
| 6,422,995 B2 | 7/2002 | Akiba |
| 6,425,857 B1 | 7/2002 | Rudischhauser |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,086 B2 | 5/2005 | Takami |
| 6,899,673 B2 | 5/2005 | Ogura |
| 6,900,829 B1 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,086 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |

(56) References Cited

U.S. PATENT DOCUMENTS

| | | |
|---|---|---|
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irian |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donomae |
| 7,893,956 B2 | 2/2011 | Ayrenschmalz |
| 7,896,802 B2 | 3/2011 | Otawara |
| 7,901,352 B2 | 3/2011 | Minami |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchimura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,976,462 B2 | 7/2011 | Wright |
| 7,995,093 B2 | 8/2011 | Takeuchi |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irian |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |

(56) References Cited

U.S. PATENT DOCUMENTS

| | | |
|---|---|---|
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,558 B2 | 9/2012 | Sato |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyamoto |
| 8,444,548 B2 | 5/2013 | Kumei |
| 8,449,456 B2 | 5/2013 | Ueno |
| 8,449,457 B2 | 5/2013 | Aizenfeld |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 8,764,642 B2 | 7/2014 | Bendele |
| 9,144,373 B2 | 9/2015 | Kaye |
| 2002/0007110 A1 | 1/2002 | Irion |
| 2002/0087047 A1 | 7/2002 | Remijan |
| 2002/0098732 A1 | 7/2002 | Shimizu |
| 2002/0109771 A1 | 8/2002 | Ledbetter |
| 2002/0109774 A1 | 8/2002 | Meron |
| 2002/0151768 A1 | 10/2002 | Akiba |
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 | 2/2003 | Murayama |
| 2003/0032860 A1 | 2/2003 | Avni |
| 2003/0036681 A1 | 2/2003 | Aviv |
| 2003/0055314 A1 | 3/2003 | Petitto |
| 2003/0083552 A1 | 5/2003 | Remijan |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihalcik |
| 2004/0073120 A1 | 4/2004 | Motz |
| 2004/0104999 A1 | 6/2004 | Okada |
| 2004/0111012 A1 | 6/2004 | Whitman |
| 2004/0133076 A1 | 7/2004 | Kobayashi |
| 2004/0138532 A1 | 7/2004 | Glukhovsky |
| 2004/0143162 A1 | 7/2004 | Krattiger |
| 2004/0158129 A1 | 8/2004 | Okada |
| 2004/0160682 A1 | 8/2004 | Miyano |
| 2004/0176661 A1 | 9/2004 | Futatsugi |
| 2004/0190159 A1 | 9/2004 | Hasegawa |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0260151 A1 | 12/2004 | Akiba |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0234296 A1 | 10/2005 | Saadat |
| 2005/0234347 A1 | 10/2005 | Yamataka |
| 2005/0251127 A1 | 11/2005 | Brosch |
| 2005/0256376 A1 | 11/2005 | Bar-Or |
| 2005/0261553 A1 | 11/2005 | Swain |
| 2005/0272975 A1 | 12/2005 | McWeeney |
| 2005/0283048 A1 | 12/2005 | Gill |
| 2005/0284491 A1 | 12/2005 | Tashiro |
| 2006/0004257 A1 | 1/2006 | Gilad |
| 2006/0047184 A1 | 3/2006 | Banik |
| 2006/0052663 A1 | 3/2006 | Koitabashi |
| 2006/0063976 A1 | 3/2006 | Aizenfeld |
| 2006/0069307 A1 | 3/2006 | Boulais |
| 2006/0069314 A1 | 3/2006 | Farr |
| 2006/0149129 A1 | 7/2006 | Watts |
| 2006/0173244 A1* | 8/2006 | Boulais ............... A61B 1/00085 600/156 |
| 2006/0183971 A1 | 8/2006 | Haviv |
| 2006/0183975 A1 | 8/2006 | Saadat |
| 2006/0189845 A1 | 8/2006 | Maahs |
| 2006/0211916 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0252994 A1 | 11/2006 | Ratnakar |
| 2006/0264704 A1 | 11/2006 | Fujimori |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0020694 A1 | 1/2007 | Pickford |
| 2007/0030345 A1 | 2/2007 | Amling |
| 2007/0049803 A1 | 3/2007 | Moriyama |
| 2007/0055100 A1 | 3/2007 | Kato |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0162095 A1 | 7/2007 | Kimmel |
| 2007/0167673 A1 | 7/2007 | Enomoto |
| 2007/0167681 A1 | 7/2007 | Gill |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0185384 A1 | 8/2007 | Bayer |
| 2007/0197875 A1 | 8/2007 | Osaka |
| 2007/0203396 A1* | 8/2007 | McCutcheon et al. ........ 600/173 |
| 2007/0206945 A1 | 9/2007 | Delorme |

(56) References Cited

U.S. PATENT DOCUMENTS

| | | |
|---|---|---|
| 2007/0208225 A1 | 9/2007 | Czaniera |
| 2007/0213590 A1 | 9/2007 | Squicciarini |
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1 | 10/2007 | Khait |
| 2007/0244353 A1 | 10/2007 | Larsen |
| 2007/0244362 A1 | 10/2007 | El-Hachem |
| 2007/0244366 A1 | 10/2007 | Murata |
| 2007/0246506 A1 | 10/2007 | Hamazaki |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1 | 2/2008 | Yasushi |
| 2008/0051628 A1 | 2/2008 | Pecherer |
| 2008/0051629 A1 | 2/2008 | Sugiyama |
| 2008/0051655 A1 | 2/2008 | Sato |
| 2008/0058595 A1 | 3/2008 | Snoke |
| 2008/0058598 A1 | 3/2008 | Ries |
| 2008/0058601 A1 | 3/2008 | Fujimori |
| 2008/0064931 A1 | 3/2008 | Schena |
| 2008/0065127 A1 | 3/2008 | Adams |
| 2008/0071290 A1 | 3/2008 | Larkin |
| 2008/0100699 A1 | 5/2008 | Hibi |
| 2008/0130108 A1 | 6/2008 | Bayer |
| 2008/0139881 A1 | 6/2008 | Cover |
| 2008/0163652 A1 | 7/2008 | Shatskin |
| 2008/0167529 A1 | 7/2008 | Otawara |
| 2008/0171910 A1 | 7/2008 | Kanazawa |
| 2008/0177139 A1 | 7/2008 | Courtney |
| 2008/0177140 A1 | 7/2008 | Cline |
| 2008/0188715 A1 | 8/2008 | Fujimoto |
| 2008/0225134 A1 | 9/2008 | Amling |
| 2008/0255425 A1 | 10/2008 | Voegele |
| 2008/0262302 A1 | 10/2008 | Azarbarzin |
| 2008/0262312 A1 | 10/2008 | Carroll |
| 2008/0312497 A1 | 12/2008 | Elmouelhi |
| 2009/0005643 A1 | 1/2009 | Smith |
| 2009/0054790 A1 | 2/2009 | Czaniera |
| 2009/0062615 A1 | 3/2009 | Yamaya |
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0161234 A1 | 6/2009 | Sasamoto |
| 2009/0163769 A1 | 6/2009 | Robertson |
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |
| 2009/0287192 A1 | 11/2009 | Vivenzio |
| 2009/0290236 A1 | 11/2009 | Wang |
| 2009/0299144 A1 | 12/2009 | Shigemori |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0013914 A1 | 1/2010 | Bettesh |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1 | 9/2010 | Bodor |
| 2010/0249496 A1 | 9/2010 | Cardenas |
| 2010/0249513 A1 | 9/2010 | Tydlaska |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0317919 A1 | 12/2010 | Takaoka |
| 2010/0317921 A1 | 12/2010 | Marple |
| 2010/0318061 A1 | 12/2010 | Derrick |
| 2010/0326703 A1 | 12/2010 | Gilad |
| 2011/0028790 A1 | 2/2011 | Farr |
| 2011/0054256 A1 | 3/2011 | Cushner |
| 2011/0112363 A1 | 5/2011 | Koga |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |

(56) References Cited

U.S. PATENT DOCUMENTS

| | | |
|---|---|---|
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |
| 2013/0253272 A1 | 9/2013 | Takahashi |
| 2013/0267778 A1 | 10/2013 | Rehe |
| 2013/0296649 A1 | 11/2013 | Kirma |
| 2013/0314521 A1 | 11/2013 | Satake |
| 2013/0317295 A1 | 11/2013 | Morse |
| 2014/0364691 A1 | 12/2014 | Krivopisk |

FOREIGN PATENT DOCUMENTS

| | | |
|---|---|---|
| CN | 1988841 | 6/2007 |
| CN | 2936129 Y | 8/2007 |
| CN | 101061940 A | 10/2007 |
| CN | 201108422 Y | 9/2008 |
| CN | 101385633 A | 3/2009 |
| CN | 101396258 | 4/2009 |
| CN | 101926171 | 12/2010 |
| CN | 102058375 A | 5/2011 |
| CN | 102058380 A | 5/2011 |
| CN | 101061940 | 6/2011 |
| CN | 201870615 U | 6/2011 |
| CN | 102469924 | 5/2012 |
| DE | 102005008153 A1 | 11/2005 |
| EP | 0029555 A2 | 6/1981 |
| EP | 543738 A1 | 5/1993 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 668738 B1 | 6/2006 |
| EP | 1685790 A1 | 8/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2321132 | 7/1998 |
| GB | 2352922 A | 2/2001 |
| JP | 2010279539 | 12/1920 |
| JP | S5551270 | 5/1980 |
| JP | 55078932 | 6/1980 |
| JP | 61055657 | 11/1986 |
| JP | S6296616 | 6/1987 |
| JP | 6359332 | 11/1988 |
| JP | H0253701 | 4/1990 |
| JP | H02188709 A | 7/1990 |
| JP | H03116801 | 12/1991 |
| JP | H04341232 | 11/1992 |
| JP | 5049000594 | 3/1993 |
| JP | H05309069 | 11/1993 |
| JP | 6105000800 | 4/1994 |
| JP | 7000000352 | 1/1995 |
| JP | 3765500 | 7/1995 |
| JP | 8122000657 | 5/1996 |
| JP | 1013007179 | 4/1998 |
| JP | 1015001113 | 6/1998 |
| JP | 11125773 | 5/1999 |
| JP | 11137512 | 5/1999 |
| JP | H11125773 | 5/1999 |
| JP | H11125773 A | 5/1999 |
| JP | 1116009340 | 6/1999 |
| JP | 1116009341 | 6/1999 |
| JP | H11253401 | 9/1999 |
| JP | 2000171727 A | 6/2000 |
| JP | 2000325306 | 11/2000 |
| JP | 2000330015 A | 11/2000 |
| JP | 2001061762 | 3/2001 |
| JP | 2001198086 | 7/2001 |
| JP | 2002000559 | 1/2002 |
| JP | 2002017667 | 1/2002 |
| JP | 2002058636 | 2/2002 |
| JP | 200265589 A | 3/2002 |
| JP | 2002065575 | 3/2002 |
| JP | 2002078675 | 3/2002 |
| JP | 2002216902 | 8/2002 |
| JP | 2002291693 | 10/2002 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004129834 | 4/2004 |
| JP | 2004205779 A | 7/2004 |
| JP | 2004354888 A | 12/2004 |
| JP | 2005013557 A | 1/2005 |
| JP | 2005058547 | 3/2005 |
| JP | 2005253543 | 9/2005 |
| JP | 2005323874 A | 11/2005 |
| JP | 2006003549 A | 1/2006 |
| JP | 2006068109 | 3/2006 |
| JP | 2006068109 A | 3/2006 |
| JP | 2006218155 | 8/2006 |
| JP | 2006280954 | 10/2006 |
| JP | 2006288758 | 10/2006 |
| JP | 2007020866 A | 2/2007 |
| JP | 2007185276 | 7/2007 |
| JP | 2008068025 | 3/2008 |
| JP | 2008118568 | 5/2008 |
| JP | 2008161569 A | 7/2008 |
| JP | 2008229204 | 10/2008 |
| JP | 2008257108 A | 10/2008 |
| JP | 2009233186 | 10/2009 |
| JP | 2009251574 | 10/2009 |
| JP | 4445647 | 4/2010 |
| JP | 2010178766 A | 8/2010 |
| WO | 9219148 A1 | 11/1992 |
| WO | 00052643 A1 | 9/2000 |
| WO | 2002045595 | 6/2002 |
| WO | 2004026125 | 4/2004 |
| WO | 2005082228 A1 | 9/2005 |
| WO | 2006073581 | 7/2006 |
| WO | 2006105932 A1 | 10/2006 |
| WO | 2007113801 A2 | 10/2007 |

(56) References Cited

FOREIGN PATENT DOCUMENTS

| | | |
|---|---|---|
| WO | 2007087421 | 11/2007 |
| WO | 2007136859 A2 | 11/2007 |
| WO | 2008012813 A1 | 1/2008 |
| WO | 2008073243 | 6/2008 |
| WO | 2008093288 | 8/2008 |
| WO | 2008139770 | 11/2008 |
| WO | 2008155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010021342 | 2/2010 |
| WO | 2010028612 | 3/2010 |
| WO | 2010045406 | 4/2010 |
| WO | 2010064506 | 6/2010 |
| WO | 2010066788 | 6/2010 |
| WO | 2010146587 | 12/2010 |
| WO | 2010146587 A1 | 12/2010 |
| WO | 2011008922 | 1/2011 |
| WO | 2011041724 | 4/2011 |
| WO | 2011083451 | 7/2011 |
| WO | 2011126812 | 10/2011 |
| WO | 2012038958 | 3/2012 |
| WO | 2012056453 | 5/2012 |
| WO | 2012077116 | 6/2012 |
| WO | 2012077117 | 6/2012 |
| WO | 2012088201 A2 | 6/2012 |
| WO | 2012103266 | 8/2012 |
| WO | 2012120507 | 9/2012 |
| WO | 2012153324 | 11/2012 |
| WO | 2013014673 | 1/2013 |
| WO | 2013024476 | 2/2013 |
| WO | 2013043704 | 3/2013 |
| WO | 2013128136 | 9/2013 |
| WO | 2013131578 | 9/2013 |
| WO | 2013144944 | 10/2013 |
| WO | 2014061023 | 4/2014 |

OTHER PUBLICATIONS

Brochure for US Endoscopy's AquaShield Water Bottle System, 2010.
First Image of an Endo Smart Cap, made by Medivators, and obtained from http://www.bymemedical.com/prod/145L.jpg and advertised at http://www.medivators.com/products/endoscopy-procedure-products/irrigation-tubing/endo-smartcap%C2%AE.
International Search Report for PCT/EP2009/066726, dated Aug. 16, 2010.
International Search Report for PCT/IL2011/000832, dated May 16, 2012.
International Search Report for PCT/IL2011/050049, dated May 15, 2012.
International Search Report for PCT/IL2011/050050, dated May 16, 2012.
International Search Report for PCT/IL2012/050037, dated Jun. 1, 2012.
International Search Report for PCT/IL2012/050274, dated Nov. 15, 2012.
International Search Report for PCT/IL2012/050299, dated Nov. 15, 2012.
International Search Report for PCT/IL2013/050840, dated Feb. 2, 2014.
International Search Report of PCT/IL10/00476 dated Sep. 27, 2010, 2 pages.
Office Action dated Apr. 3, 2014 for U.S. Appl. No. 13/413,141.
Office Action dated Feb. 24, 2014 for U.S. Appl. No. 13/190,968.
Office Action dated Feb. 27, 2014 for U.S. Appl. No. 13/557,114.
Office Action dated Jul. 1, 2014 for U.S. Appl. No. 13/655,120.
Office Action dated Jul. 31, 2014 for U.S. Appl. No. 13/713,449.
Office Action dated Jun. 12, 2014 for U.S. Appl. No. 13/713,466.
Office Action dated Mar. 28, 2014 for U.S. Appl. No. 13/413,252.
Office Action dated May 27, 2014 for U.S. Appl. No. 13/212,627.
Office Action dated May 30, 2014 for U.S. Appl. No. 13/119,032.
Office Action dated May 9, 2014 for U.S. Appl. No. 13/413,059.
Notice of Allowance dated Jun. 8, 2015 for U.S. Appl. No. 13/984,028.
Notice of Allowance dated Jun. 8, 2015 for U.S. Appl. No. 13/413,252.
Prosecution File History for U.S. Appl. No. 13/190,968; Jul. 26, 2011 through Jun. 17, 2015.
Notice of Allowance dated Jun. 17, 2015 for U.S. Appl. No. 13/190,968.
Corrected European Search Opinion for EP14186113.8, dated Apr. 29, 2015.
Extended European Search Report for EP14186113.8, dated Apr. 1, 2015.
First Office Action for CN 2012800368972, dated Jun. 1, 2015.
Office Action dated Aug. 19, 2015 for U.S. Appl. No. 13/713,466.
Office Action dated Aug. 19, 2015 for U.S. Appl. No. 13/713,449.
Office Action dated Aug. 4, 2015 for U.S. Appl. No. 13/557,114.
Office Action dated Aug. 5, 2015 for U.S. Appl. No. 13/212,627.
Office Action dated Aug. 6, 2015 for U.S. Appl. No. 13/119,032.
Office Action dated Jul. 21, 2015 for U.S. Appl. No. 13/992,021.
Office Action dated Nov. 3, 2015 for U.S. Appl. No. 13/992,014.
Office Action for Chinese Patent Application No. 201180067259.2, dated May 29, 2015.
Extended European Search Report for EP11847191.1, dated Jan. 15, 2016.
Examination Report for Canadian Patent Application No. CA2765559, dated Jan. 18, 2016.
Examination Search Report for Canadian Patent Application No. CA2765559, dated Jan. 18, 2016.
Extended European Search Report for EP11846069.0, dated Apr. 24, 2014.
Extended European Search Report for EP12817452.1, dated Mar. 9, 2015.
First Office Action for Chinese Patent Applicatio No. CN201380053351.2, dated Mar. 2, 2016.
Notice of Allowance dated Dec. 15, 2014 for U.S. Appl. No. 13/713,466.
Notice of Allowance dated Dec. 15, 2015 for U.S. Appl. No. 13/713,466.
Notice of Allowance dated Dec. 23, 2015 for U.S. Appl. No. 13/992,021.
Office Action dated Aug. 27, 2015 for U.S. Appl. No. 13/655,120.
Office Action dated Jan. 12, 2016 for U.S. Appl. No. 13/713,466.
Office Action dated Nov. 16, 2015 for U.S. Appl. No. 13/557,114.
Office Action dated Nov. 24, 2015 for U.S. Appl. No. 13/413,059.
Office Action dated Oct. 7, 2015 for U.S. Appl. No. 13/882,004.
Office Action for Chinese Patent Application No. 201280038808.8, dated May 20, 2015.
Office Action for Japanese Patent Application No. 2013-535586, dated Sep. 24, 2015.
Office Action for Japanese Patent Application No. 2013-542668, dated Oct. 1, 2015.
Second Office Action for Chinese Patent Applicatio No. CN201280038808.8, dated Feb. 25, 2016.
Second office action for Chinese Patent Application No. 201180062736.6, dated Oct. 12, 2015.
Supplementary European Search Report for EP118471911, dated Jan. 16, 2015.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action for Japanese Patent Application No. JP2014-522214, dated Apr. 26, 2016.
Office Action for Japanese Patent Application No. JP2014-525562, dated Apr. 26, 2016.
Second image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.
Office Action dated Jun. 30, 2016 for U.S. Appl. No. 13/655,120.
Second Office Action for Chinese Patent Application No. 201180067259.2, dated Mar. 30, 2016.

(56) References Cited

OTHER PUBLICATIONS

Extended European Search Report for application No. EP12755186, completed on May 23, 2016.
Supplementary European Search Report for EP13847670, completed on May 19, 2016.
Office Action dated Apr. 28, 2016 for U.S. Appl. No. 13/992,014.
Notice of Allowance dated Aug. 26, 2016 for U.S. Appl. No. 13/212,627.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Notice of Allowance dated Nov. 9, 2016 for U.S. Appl. No. 13/557,114.
Third Office Action for Chinese Patent Application No. 201180067259.2, dated Oct. 21, 2016.
Office Action for Chinese Patent Application No. 201180062736.6, dated Dec. 23, 2016.
Office Action for Japanese Patent Application No. 2016-105009, dated Jan. 16, 2017.
Office Action for Chinese Patent Application No. 201380053351.2, dated Dec. 13, 2016.
First Office Action for EP11847191.1, dated Feb. 21, 2017.
Office Action dated Mar. 21, 2017 for U.S. Appl. No. 13/992,014.
Notice of Allowance dated Apr. 18, 2017 for U.S. Appl. No. 13/713,449.
Examination Report for EP11846069.0, dated Feb. 21, 2017.
Extended European Search Report for EP11826512.3, dated Apr. 6, 2017.
Office Action dated May 23, 2017 for U.S. Appl. No. 13/655,120.

\* cited by examiner

MULTI-CAMERA ENDOSCOPE HAVING FLUID CHANNELS

RELATED APPLICATION DATA

This application is a U.S. National Stage of International Application No. PCT/IL2011/000745, filed Sep. 20, 2011, which claims the benefit of U.S. Provisional Application No. 61/384,354, filed Sep. 20, 2010, the contents of each of which are herein expressly incorporated by reference for all purposes.

FIELD OF THE INVENTION

Embodiments of the disclosure relate to a multi-camera endoscope having fluid channels.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the bodys natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Endoscopes, such as colonoscopes, that are currently being used, typically have a front camera for viewing the internal organ, such as the colon, an illuminator, a fluid injector for cleaning the camera lens and sometimes also the illuminator and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmit light, generated remotely, to the endoscope tip section. The use of light-emitting diodes (LEDs) for illumination is also known.

Among the disadvantages of such endoscopes, are their limited field of view and their complicated packing of all the required elements, such as electronics and fiber optics together with fluid carrying elements in the small sized endoscope tip section.

There is thus a need in the art for endoscopes, such as colonoscopies, that allow a broader field of view and also enable the function of all necessary elements in the tip section.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

In accordance with some embodiments of the invention, there is provided a tip section of a multi-camera endoscope, the tip section comprising: a unitary fluid channeling component adapted to channel fluid for insufflations and/or irrigation (I/I), the unitary fluid channeling component comprising: a proximal opening adapted to receive a fluid tube, the proximal opening being in fluid flow connection with a front fluid (I/I) channel and a side fluid channel.

The fluid tube may include a gas tube and a liquid tube separated from each other or combined into one tube. The front fluid channel may lead to a front opening at a distal end in the unitary fluid channeling component; and the side fluid channel may lead to a left side opening and to a right side opening in the unitary fluid channeling component. The front fluid channel may extend along the length of the unitary fluid channeling component. The side fluid channel may be essentially perpendicular to the length of the unitary fluid channeling component.

The front opening may be adapted to receive a fluid injector and wherein the side openings are adapted to receive fluid injectors. The front channel, the side channel or both may be drilled in the unitary fluid channeling component. The front fluid channel, the side fluid channel or both may be partially internal and partially external to unitary fluid channeling component.

The unitary fluid channeling component may further include a working channel adapted for the insertion of a medical tool. The unitary fluid channeling component may further include a jet fluid channel adapted to clean a body cavity into which the endoscope is inserted. The unitary fluid channeling component may further include a groove or a channel for guiding a cable.

In accordance with some embodiments of the invention, there is provided a tip section of a multi-camera endoscope, the tip section comprising: a unitary fluid channeling component adapted to channel fluid for insufflations and/or irrigation, the unitary fluid channeling component comprising: a first proximal opening adapted to receive a first fluid tube and connected to a front fluid (I/I) channel; and a second proximal opening adapted to receive a second fluid tube and connected to a first side fluid (I/I) channel, wherein any of the first and second fluid tubes are adapted to transfer liquid, gas or a combination thereof to the tip section.

The front fluid channel may lead to a front opening at a distal end in the unitary fluid channeling component; and the side fluid channel may lead to one or more side opening in the unitary fluid channeling component. The front and side openings may be adapted to receive fluid injectors. The front fluid channel may extend along the length of the unitary fluid channeling component. The first side fluid channel may lead to a left side opening and to a right side opening in the unitary fluid channeling component and may be essentially perpendicular to the length of the unitary fluid channeling component.

The unitary fluid channeling component may further include a third proximal opening adapted to receive a third fluid tube connected to a second side fluid (I/I) channel.

Any of the side front channel and the one or more side channel may be drilled in the unitary fluid channeling component. Any of the front fluid channel and the one or more side fluid channels may be partially internal and partially external to unitary fluid channeling component.

The unitary fluid channeling component may further include a working channel adapted for the insertion of a medical tool. The unitary fluid channeling component may further include a jet fluid channel adapted to clean a body cavity into which the endoscope is inserted. The unitary fluid channeling component may further include a groove or a channel for guiding a cable.

The tip section may have a diameter of about 17 mm or less. The tip section may have a diameter of about 12 mm or less. The tip section may have a diameter of about 10 mm or less.

In accordance with some embodiments of the invention, there is provided an endoscope comprising a tip section as described herein.

In accordance with some embodiments of the invention, there is provided a manifold for irrigation and/or insufflation (I/I) fluids, for providing gas such as $CO_2$ or air for inflating the colon (or other body cavity) during diagnostic or minimally invasive procedure, such as colonoscopy, and/or for providing cleaning liquid, for example water or saline, for cleaning optical front surfaces in an endoscope having at least one forward looking camera and one or more side looking cameras while maintaining small size of the tip section of the endoscope.

According to a first exemplary embodiment of the current invention, proximal opening for gas tube and liquid tube is directly opened to I/I channel manifold, located entirely within the tip section cylinder, the manifold comprises:

According to the first exemplary embodiment of the current invention, proximal opening for gas tube and liquid tube is directly opened to I/I channel manifold, entirely within the cylinder which comprises:

a) a right I/I opening, connected to the proximal opening, and into which right I/I injector is inserted;

b) a front I/I channel connected to proximal opening, and leading to front I/I opening into which front I/I injector is inserted; and c) a cross I/I channel, connected to the proximal opening, and which is opened to left I/I opening a into which left I/I injector is inserted.

According to a second exemplary embodiment of the current invention, proximal opening for gas tube and liquid tube within a cylinder in the endoscope's tip section is opened to I/I channel manifold which comprises:

a) a right I/I opening into which right I/I injector is inserted;

b) a front I/I channel within the cylinder, connected to front I/I opening into which front I/I injector is inserted; and c) a hole, connected to a groove on the surface of the cylinder which is opened to left I/I a into which left I/I injector is inserted.

According to the third exemplary embodiment of the current invention proximal opening for gas tube and liquid tube within a cylinder in the endoscope's tip section is opened to right I/I opening and through it to a I/I manifold which comprises:

a) a right I/I opening into which right I/I injector is inserted;

b) a front I/I channel within the cylinder, connected to front I/I opening into which front I/I injector is inserted; and c) a groove on the surface of the cylinder, which receives cleaning fluids from right I/I opening, and is opened to left I/I opening into which left I/I injector is inserted.

According to a forth embodiment of the current invention, proximal opening for gas tube and liquid tube within a cylinder in the endoscope's tip section is opened to right I/I opening and through it to a I/I manifold which comprises:

a) a right I/I opening into which right I/I injector is inserted;

b) a groove on the surface of the cylinder which receives cleaning fluids from right I/I opening, and is opened to left I/I opening into which left I/I injector is inserted; and c) a front I/I groove on the surface of the cylinder, receiving I/I fluids from the groove, and connected to front I/I opening into which front I/I injector is inserted.

According to a fifth embodiment of the current invention, proximal opening for gas tube and liquid tube within a cylinder in the endoscope's tip section is opened to a right I/I opening and connected through hole to I/I manifold which comprises:

a) a right I/I opening into which right I/I injector is inserted;

b) a groove on the surface of the cylinder which receives cleaning fluids via a hole connected to the proximal opening, and is opened to left I/I opening is into which left I/I injector is inserted; and c) a front I/I groove on the surface of the cylinder, receiving I/I fluids from the hole, and connected to front I/I opening into which front I/I injector is inserted.

According to a sixth embodiment of the current invention, proximal opening for gas tube and liquid tube within a cylinder in the endoscope's tip section is opened to a hole and through it to a I/I manifold which comprises:

a) a grove on the surface of the cylinder which receives cleaning fluids from proximal opening via the hole; and is connected to right I/I opening into which right I/I injector is inserted;

b) the same groove is connected to left I/I opening, to which left I/I injector is inserted; and c) a front I/I groove, receiving I/I fluids from the groove, and connected to front I/I opening into which front I/I injector is inserted.

According to an exemplary embodiment of the current invention, the medical endoscope tip section is less than 17 mm in diameter In some embodiments the medical endoscope tip section is less than 12 mm in diameter More details and features of the current invention and its embodiments may be found in the description and the attached drawings.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

DETAILED DESCRIPTION

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

Figure 1A:
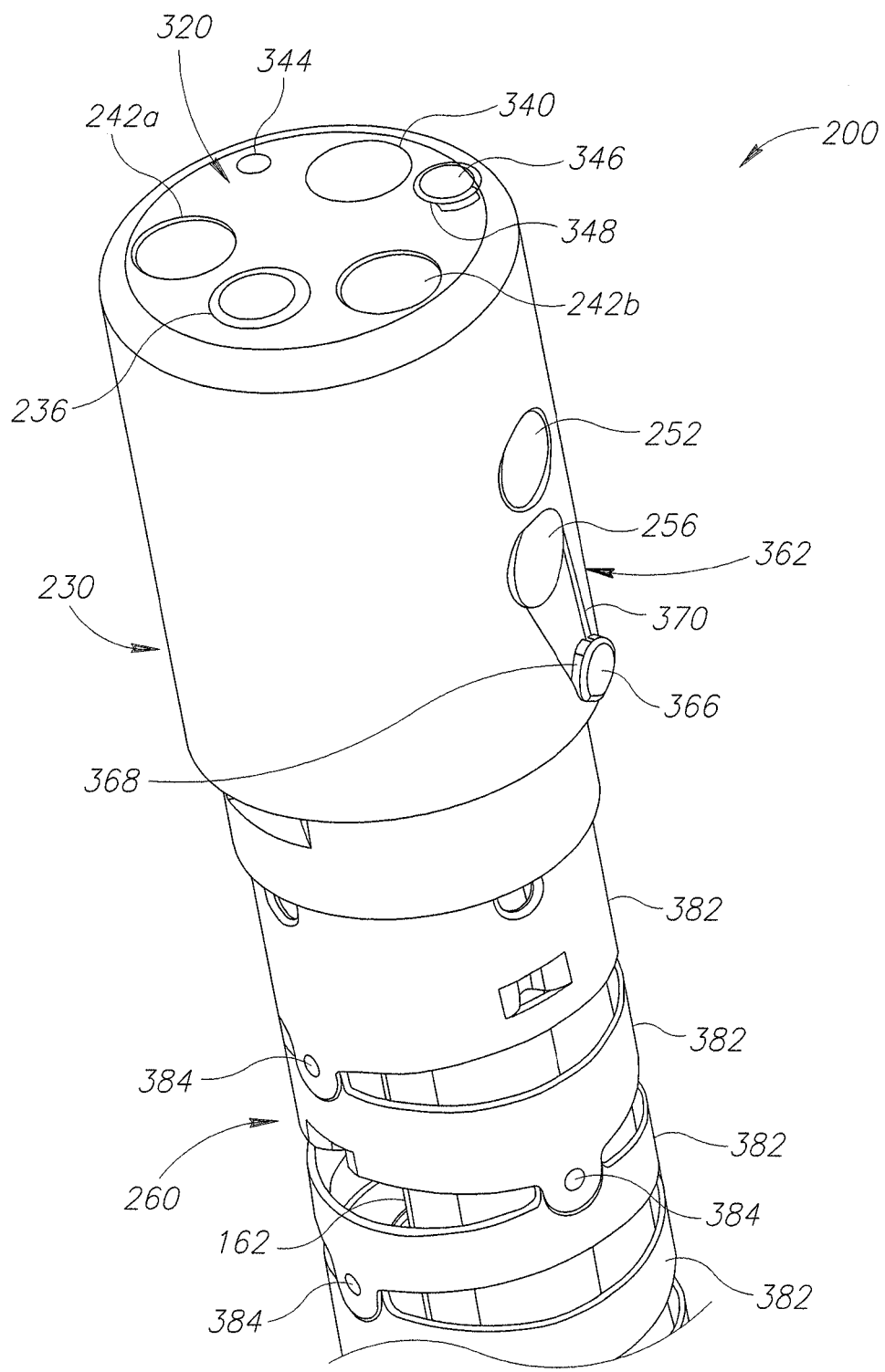
FIG. 1a schematically depicts an external isometric view of an endoscope having multiple fields of view according to an exemplary embodiment of the current invention.

FIG. 1a schematically depicts an external isometric view of an endoscope 200 having multiple fields of view according to an exemplary embodiment of the current invention.

According to an exemplary embodiment of the current invention, tip section 230 of endoscope 200 comprises at least a forwards looking TV camera and at least one side looking TV camera. Tip section 230 is turnable by way of flexible shaft 260 (which may also be referred to as a bending section, for example a vertebra mechanism).

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

FIG. 1a shows front camera element 236 of forwards looking camera 116 (seen in FIG. 2b) on the front face 320 of tip section 230. Optical axis of forwards looking camera 116 is substantially directed along the long dimension of the endoscope. However, since forwards looking camera 116 is typically a wide angle camera, its Field Of View (FOV) may include viewing directions at large angles to its optical axis. Additionally, optical windows 242a and 242b of LEDs 240a and 240b (seen for example in FIG. 2b) are also seen on front face is 320 of tip section 230. It should be noted that number of LEDs used for illumination of the FOV may vary. Distal opening 340 of working channel 262 (seen for example in FIG. 1b) is preferably located on front face 320 of tip section 230, such that a surgical tool inserted through working channel tube 162, and through working channel 262 in the endoscope's tip section and deployed beyond front face 320 may be viewed by forwards looking camera 116.

Distal opening 344 of a jet fluid channel is preferably also located on front face 320 of tip section 230. Distal opening 344 of a jet fluid channel may be used for providing high pressure jet of fluid such as water or saline for cleaning the walls of the body cavity.

I/I injector 346 having a nozzle 348 aimed at front camera element 236 may be used for injecting fluid (liquid and/or gas) to wash contaminants such as blood, feces and other debris from front camera element 236 of forwards looking camera. Optionally the same injector is used for cleaning both front camera element 236 and one or both optical windows 242a and 242b. I/I injector 346 may be fed by fluid such as water and/or gas which may be used for cleaning and/or inflating a body cavity.

Figure 2A:
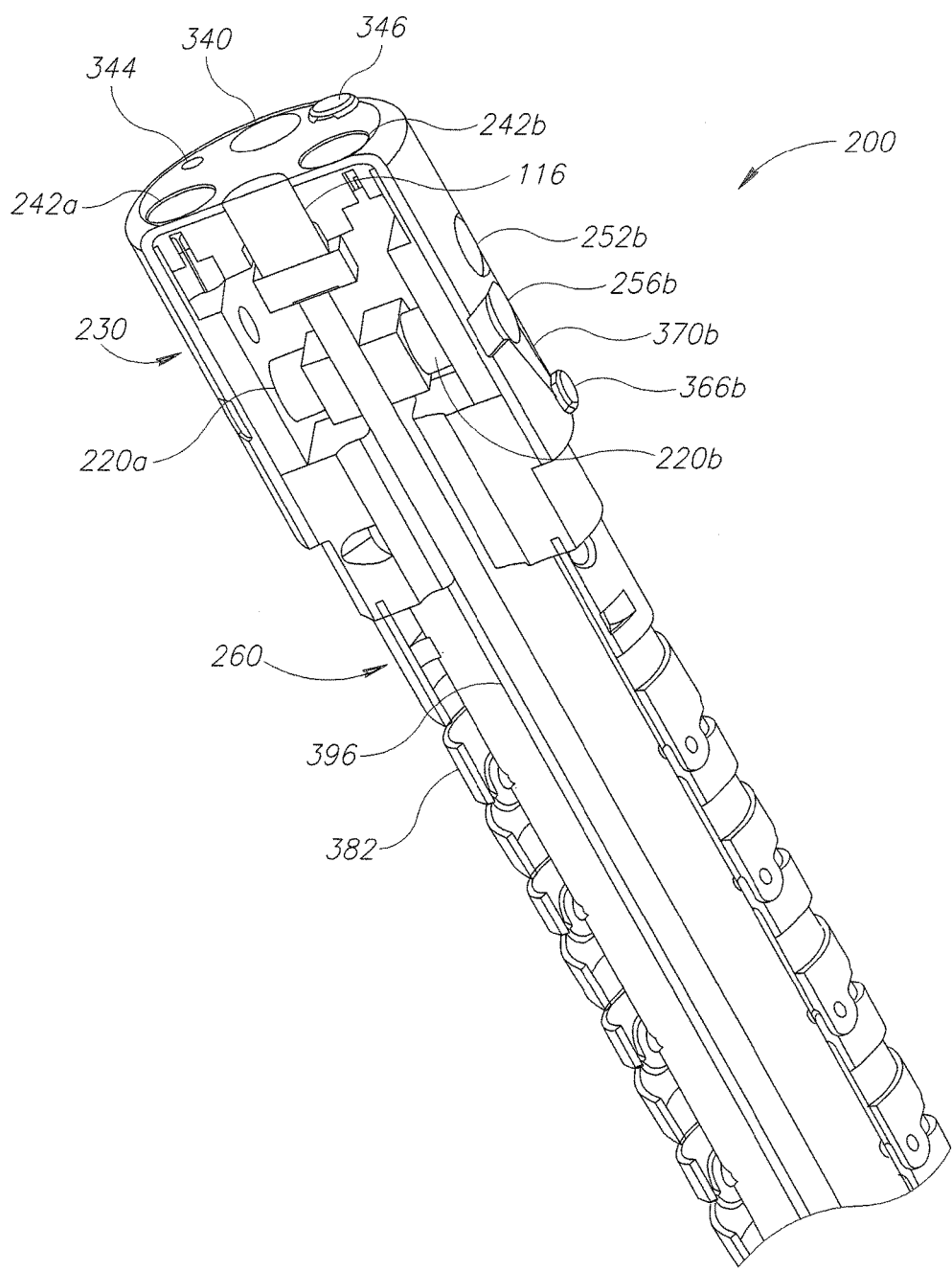
FIG. 2a schematically depicts an isometric cross section of an endoscope having multiple fields of view, for use within bodily cavity according to an exemplary embodiment of the current invention.

Visible on the side wall 362 of tip section 230 is the side camera (side looking camera) element 256 of side looking camera 220 (two such cameras are seen in FIG. 2a) and optical window 252 of LED 250. Optical axis of side looking camera 220 is substantially directed perpendicular to the long dimension of the endoscope. However, since side looking camera 220 is typically a wide angle camera, its field of view may include viewing directions at large angles to its optical axis.

I/I injector 366 having a nozzle 368 aimed at side camera element 256 may be used for injecting fluid to wash contaminants such as blood, feces and other debris from side camera element 256 of side looking camera. The fluid may include gas which may be used for inflating a body cavity. Optionally the same injector is used for cleaning both side camera element 256 and optical windows 252. It is noted that according to some embodiments, the tip may include more than one window and LEDs, on the side and more than one window and LEDs in the front (for example, two windows and two LEDs on the side and three windows and three LEDs in the front). The I/I injectors are configured to clean all or a part of these windows/LEDs). I/I injectors 346 and 366 may be fed from same channel. An optional groove 370 helps directing the cleaning fluid from nozzle 368 towards side camera element 256. Groove 370 may be beneficial when side wall 362 is near or pressed against the rectal wall. Optionally, I/I injector 366 may be at least partially recessed in groove 370, thus reducing the maximum diameter of tip section 230 and reduce the risk of injury to the rectal wall due to friction with I/I injector 366.

In the depicted embodiment, flexible shaft 260 is constructed of a plurality of links 382 connected to each other by pivots 384. Links 382 allows pushing, pulling and rotating the endoscope while pivots 384 provide limited flexibility. The shaft is preferably covered with an elastic sheath (removed from this figure for simplification purposes). The lumen in links 382 holds the working channel tube 162. Not seen in this figure are the jet channel connected to distal opening 344, optional cleaning fluid channel and electrical cables supplying power to the LEDs and cameras and transmitting video signals from the camera. Generally, the shaft also comprises mechanical actuators (not seen), for example cables attached to the links for directing and aiming the tip section during use.

It should be noted that while only one side looking camera is seen in FIG. 1a, preferably at least two side looking cameras may be located within tip section 230. When two side looking cameras are used, the side looking cameras are preferably installed such that their field of views are substantially opposing. However, different configurations and number of side looking cameras are possible within the general scope of the current invention.

Figure 1B:
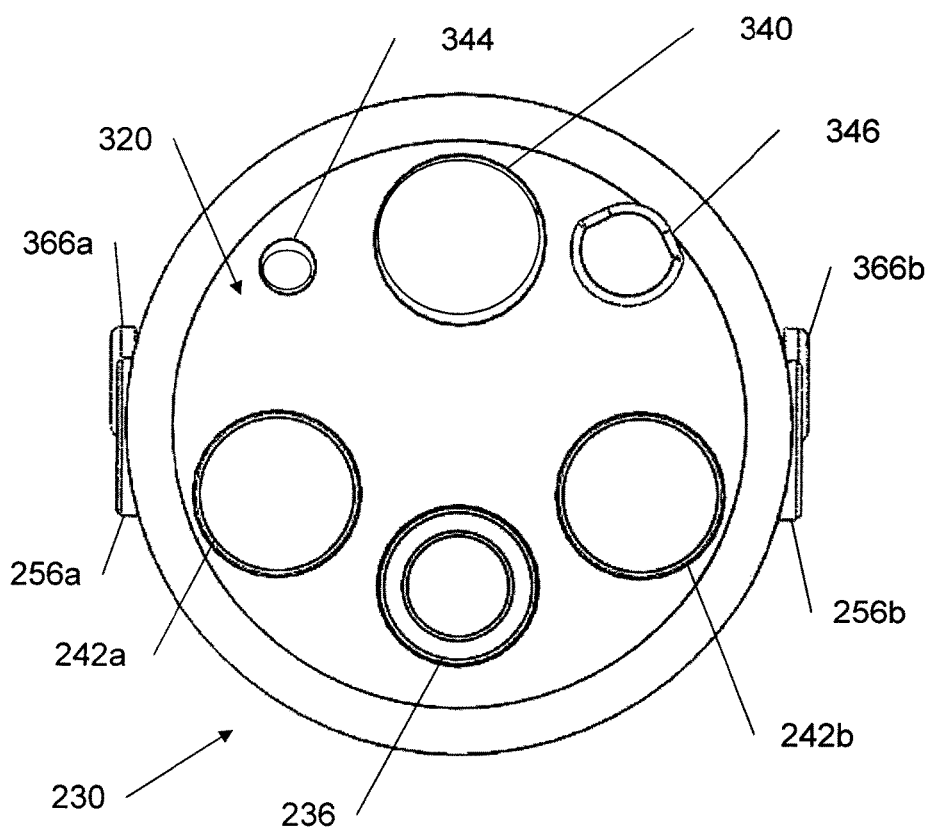
FIG. 1b schematically depicts a front view of an endoscope having multiple fields of view according to an exemplary embodiment of the current invention.

FIG. 1b schematically depicts a front view of tip section 230 of endoscope 200 having multiple fields of view according to an exemplary embodiment of the current invention.

According to an exemplary embodiment of the current invention, tip section 230 of endoscope 200 comprises at least a forwards looking TV camera and at least two side looking TV cameras. FIG. 1b shows a front camera element 236 of forwards looking camera 116 on the front face 320 of tip section 230. Additionally, optical windows 242a and 242b of LEDs 240a and 240b are also seen on front face 320 of tip section 230. Distal opening 340 of working channel and distal opening 344 of a jet channel are preferably also located on front face 320 of tip section 230. I/I injector 346 having a nozzle 348 is also visible in this view.

Additionally, I/I injectors 366a and 366b aimed at side looking camera element 256a and 256b respectively may be used for injecting fluid (the term "fluid" may also include gas and/or liquid) to wash contaminants such as blood, feces and other debris from side camera elements 256a and 256b of side looking cameras. According to some embodiments, the injectors may supply liquid for cleaning any of the tip elements (such as any camera element, windows, LEDs, and other elements).

Figure 1C:
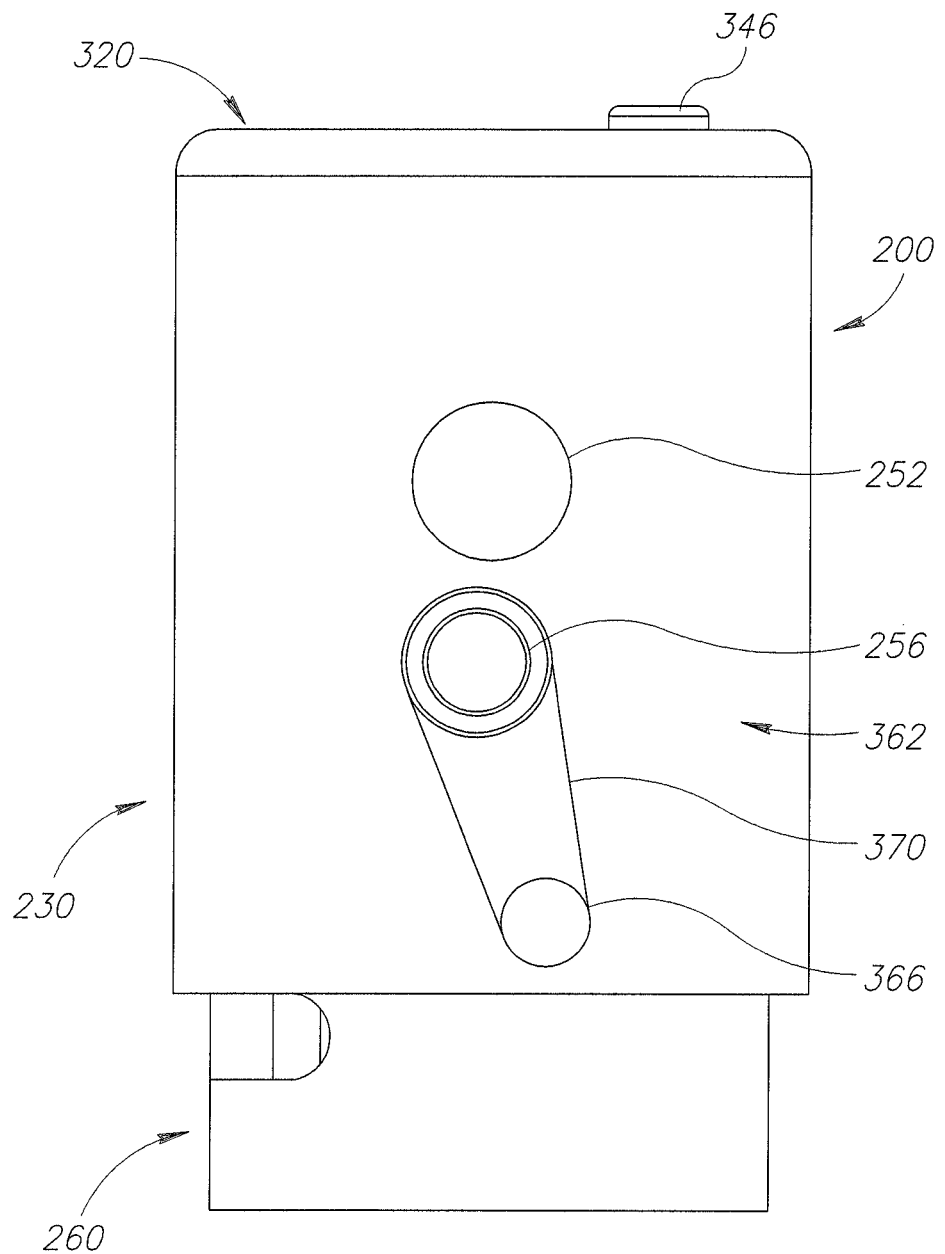
FIG. 1c schematically depicts a side view of endoscope having multiple fields of view according to an exemplary embodiment of the current invention.

FIG. 1c schematically depicts a side view of endoscope 200 having multiple fields of view according to an exemplary embodiment of the current invention.

FIG. 1c shows side camera element 256 of side looking camera 220, optional groove 370 and optical window 252 on the side wall 362 of tip section 230. I/I injectors 346 and 366 are also visible in this view.

FIG. 2a schematically depicts a cross section isometric view of an endoscope 400 having multiple fields of view according to another exemplary embodiment of the current invention.

According to an exemplary embodiment of the current invention, tip section 430 of endoscope 200 comprises at least a forwards looking TV camera 116 and two side looking cameras 220a and 220b.

Optical windows 242a and 242b of LEDs used for forward illumination are also seen on front face of tip section 230.

Distal opening 340 of working channel is preferably located on front face of tip section 230 such that a surgical tool inserted through the working channel 262 and deployed beyond front face may be viewed by forwards looking camera 116.

Distal opening 344 of a jet channel is preferably also located on front face of tip section 230.

I/I injector 346 having a nozzle aimed at front camera element of camera 116 may be used for injecting fluid (gas and/or water) to wash contaminants such as blood, feces and other debris from front camera element of forwards looking camera 116 and to inflate a body cavity (such as a colon) into which the endoscope (such as colonoscope) is inserted. Optionally the same injector is used for cleaning the front camera element and one or both optical windows 242a and 242b. I/I injector 346 may receive fluid from a fluid channel or may be fed by a dedicated cleaning fluid channel.

Visible on right hand side of tip section 230 is side camera element 256b of side looking camera 220b and optical window 252b of side illuminating LED.

I/I injector 366b having a nozzle aimed at side camera element 256b may be used for injecting fluid to wash contaminants such as blood, feces and other debris from side camera element 256b of side looking camera 220b and to inflate a body cavity (such as a colon) into which the endoscope (such as a colonoscope) is inserted. Optionally the same injector is used for cleaning both front camera element 256b and optical windows 252b. An optional groove 370b helps directing the cleaning fluid from I/I injector 366b towards side camera element 256b.

Although not seen in this figure, it is understood that equivalent elements 366a, 370a, 256a and 252a are present on the left hand side of tip section 230.

Preferably, all the I/I injectors 346 and 366 are fed from same conduits.

In the depicted embodiment, flexible shaft (vertebra mechanism) 260 is is constructed of a plurality of links 382 (only one is marked for simplification). Electrical cable 396 within shaft 260 is seen connected to cameras 116, 220a and 220b. The same or separate electrical cable is used to power the LEDs.

Figure 2B:
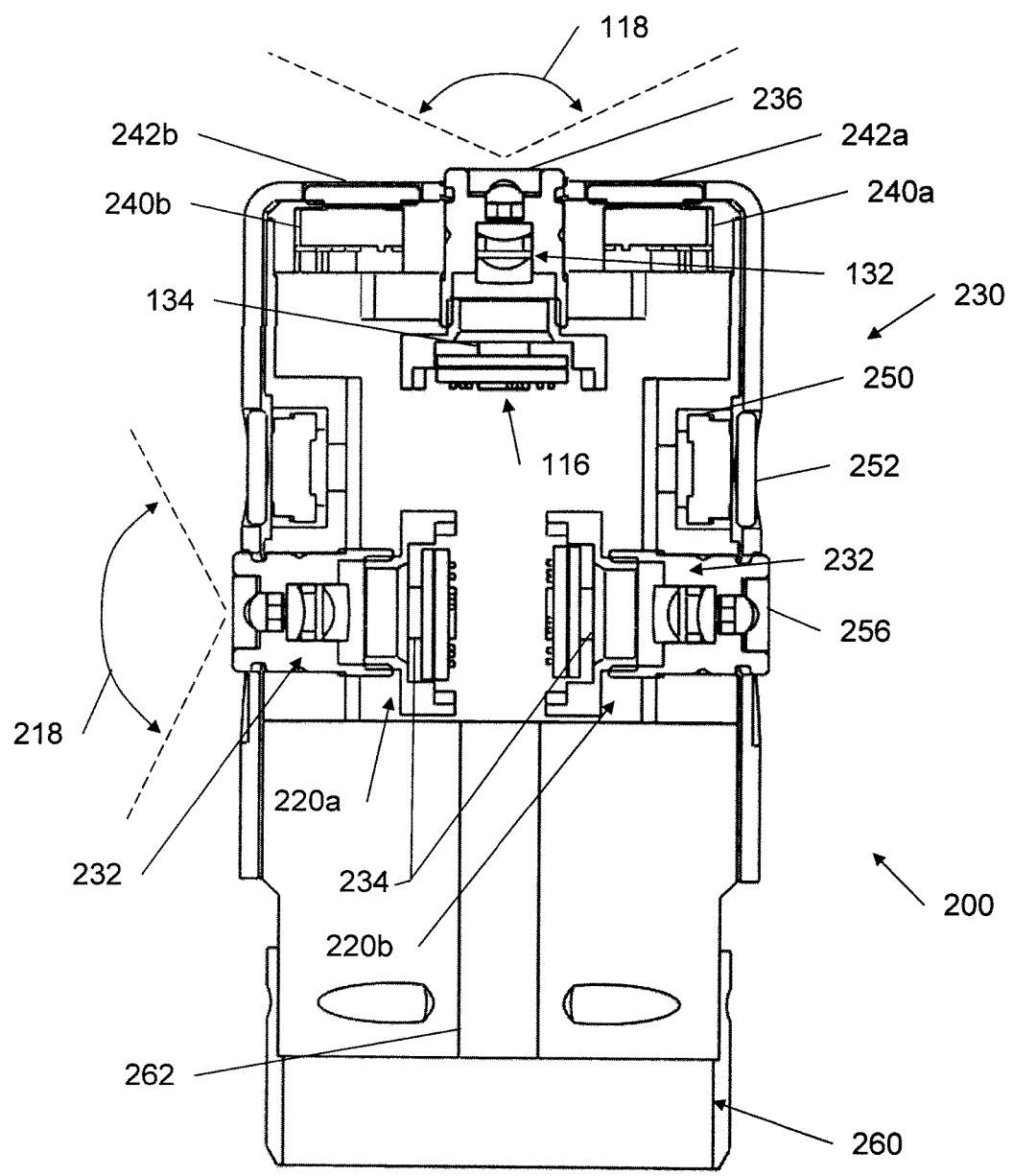
FIG. 2b schematically depicts a cross section of an endoscope tip section having multiple fields of view showing some details of the tip section according to an exemplary embodiment of the current invention.

FIG. 2b schematically depicts a cross section of an endoscope 200 having multiple fields of view showing some details of the tip section 230 according to an exemplary embodiment of the current invention.

According to embodiments of the current invention, tip section 230 of endoscope 200 comprises at least a forwards looking TV camera 116 and two side looking cameras 220a and 220b. Each of cameras 116 and 220 is provided with an optical imaging system such as lens assemblies 132 and 232 respectively and solid state detector arrays 134 and 234 respectively. Front camera elements 236 and 256 of cameras 116 and 220 respectively may be a flat protective window, but preferably an optical element used as part of the imaging systems 134 and 132 respectively. Optionally, cameras 116 and 220 are similar or identical, however different camera designs may be used, for example, field of views 118 and 218 may be different. Additionally or alternatively, other camera designs parameters such as: resolution, light sensitivity, pixel size and pixel number, focal length, focal distance and depth of field may be selected to be same or different.

Light is provided by Light Emitting Diodes (LED) that illuminates the field of views. Preferably, white light LEDs are used.

In the depicted embodiment, field of view 118 of forwards looking camera 116 is illuminated by two LEDs 240a and 240b located within the endoscope tip section 230 and protected by optical window 242a and 242b respectively. According to some embodiments, forwards looking camera 116 may be illuminated by any other number of LEDs, for example, 1, 3, 4, 5 LEDs)

Similarly, in the depicted embodiment, field of views of side looking camera 220 is illuminated by a single LED 250 located within the endoscope tip section 230 and protected by optical window 252. According to some embodiments, side looking camera 220 may be illuminated by any other number of LEDs, for example, 2, 3, 4, 5 LEDs)

It should be noted that number of LED light sources and their position in respect to the cameras may vary within the scope of the current invention. For example few LEDs may be positioned behind the same protective window, a camera and an LED or plurality of LED may be located behind the same protective window, etc.

Tip section 230 of endoscope 200 is located at the distal end of a flexible shaft 260. Similarly to shafts of the art, shaft 260 comprises a working channel 262 for insertion of surgical tools. Additionally, shaft 260 may comprises channels for irrigation, insufflation, suction and supplying liquid for washing the external elements of the cameras and optionally the light sources.

Figure 2C:
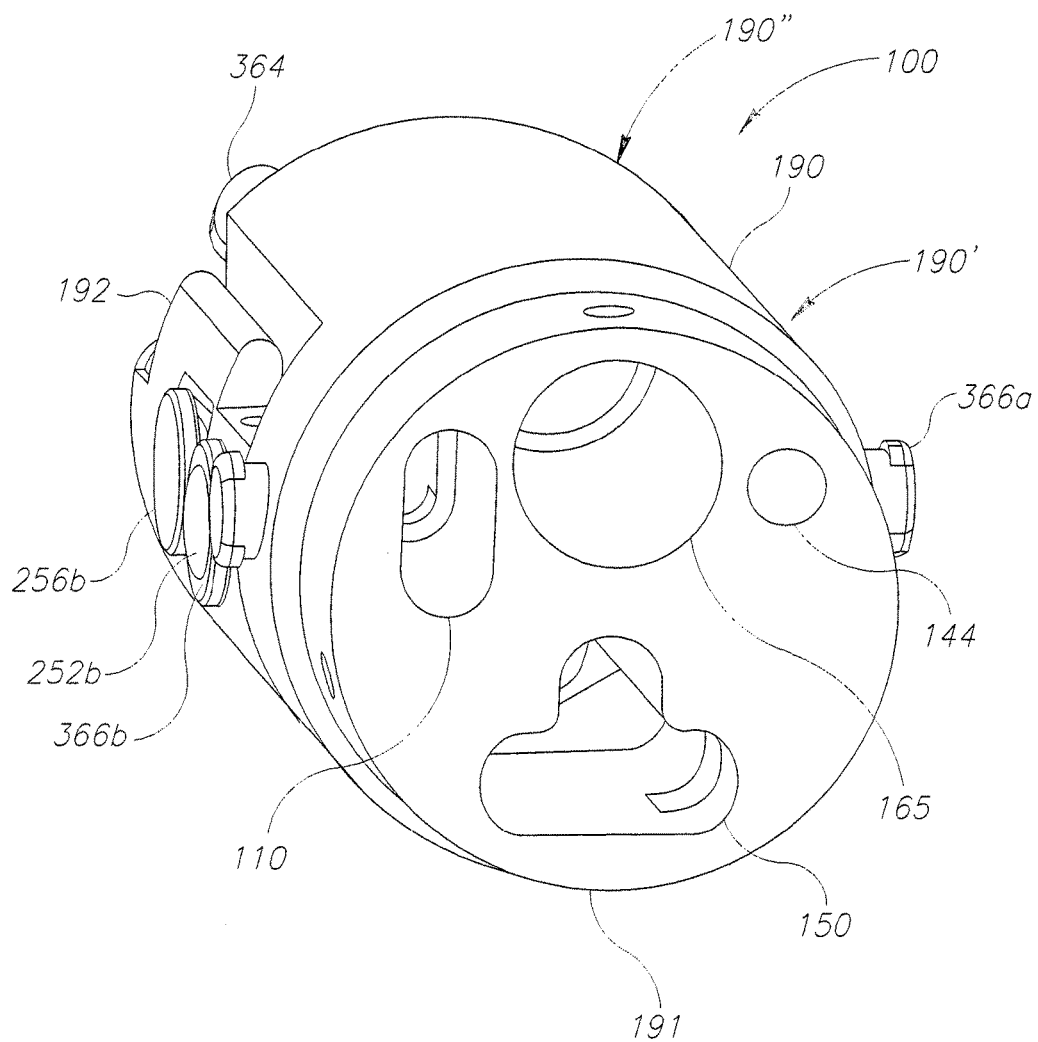
FIG. 2c schematically depicts an isometric proximal view of an inner part of an endoscope tip section according to an exemplary embodiment of the current invention.

FIG. 2c schematically depicts an isometric proximal view of an inner part of a tip section of an endoscope according to an exemplary embodiment of the current invention showing the entrances of various channels in the inner part of a tip section.

Inner part 100 of a tip section is located within the tip section and may be used for holding in place the components of the endoscope's tip section such as I/I injectors 364, 366a and 366b; cameras, lenses and other elements. A cover (not seen in this figure) is placed over inner part 100. Some elements, for example 111 injectors 364 and 366 (and optionally side camera element 256b) may be assembled after the cover was placed.

Inner part 100 of a tip section may comprise of several parts. In the depicted embodiment inner part 100 of the tip section comprises: unitary fluid channeling component 190, central section 192 and front section 194 (examples of which are seen in some of the following figures). Unitary fluid channeling component 190 may be made of a metal or any other material, such as a polymer, a composite material or any other appropriate material or combination of materials. Unitary fluid channeling component 190, according to some embodiments, may generally include two parts: a proximal fluid channeling component section 190' and a distal fluid channeling component section 190". Proximal fluid channeling component section 190' may have an essentially cylindrical shape. Distal unitary channeling component section 190" may partially continue the cylindrical shape of proximal fluid channeling component section 190' and may have a shape of a partial cylinder (optionally elongated partial cylinder), having only a fraction of the cylinder (along the height axis of the cylinder), wherein another fraction of the cylinder (along the height axis of the cylinder) is missing. (Distal fluid channeling component section 190", which may be integrally formed as a unitary block with proximal fluid channeling component section 190'. The height of distal fluid channeling component section 190" may by higher than that of proximal fluid channeling component section 190'. In the case of distal fluid channeling component section 190", the shape of the partial cylinder (for example, partial cylinder having only a fraction of a cylinder shape along one side of the height axis) may provide a space to accommodate central section 192. Central section 192 may include electronics and optical components, such as light means (LEDs for example), cameras (CCD or CMOS, for example) lenses, and other elements. This configuration of inner part 100 of the tip section may thus be adapted to separate the fluid channels and work channel, which are located in fluid channeling component 190 from the sensitive electronic and optical parts which are located in central section 192. This paragraph may apply to any one of main bodies 190a-190f.

On the proximal surface 191 of unitary fluid channeling component 190 is proximal opening 144 of the jet fluid channel leading to distal opening 344 of the jet channel. Fluid tube (not shown in this figure for simplification purposes) may be inserted into, and affixed to distal opening 144 of the jet fluid channel. The jet fluid tube is threaded through flexible shaft 260 and is used for delivering fluid to the body cavity.

On the proximal surface 191 of unitary fluid channeling component 190 is proximal opening 165 of the working channel 262 leading to distal opening 340 of the working channel. Working channel tube/tools may be inserted into, and optionally affixed to proximal opening 165 of the working channel. The working channel 162 is threaded through flexible shaft 260 and is used for delivering surgical tools to the body cavity. Working channel 162 may also be used for suction of fluid from the body cavity.

On the proximal surface 191 of unitary fluid channeling component 190 is the electric cable opening 150 for electrical cable 396 (seen for example in FIG. 2a). Electrical cable 396 is connected at its distal end to the electronic components such as cameras and light sources in the endoscope's tip section. Electrical cable 396 is threaded through flexible shaft 260 and is used for delivering electrical power and command signals to the tip section and transmitting video signal from the cameras to be displayed to the user.

Figure 3A:
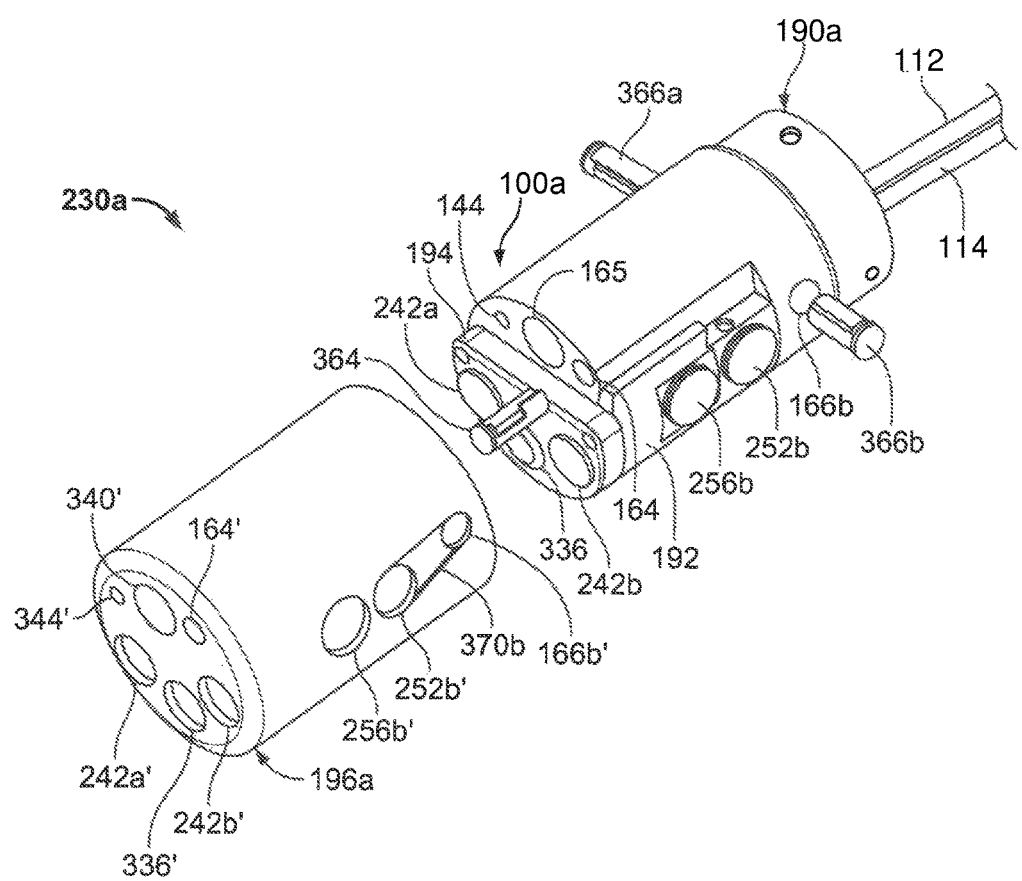
FIG. 3a schematically depicts a partially disassembled tip section of an endoscope having I/I channels manifold internal to a unitary fluid channeling component, according to a first exemplary embodiment of the current invention.

On the proximal surface 191 of unitary fluid channeling component 190 is the I/I tubes proximal opening 110 for gas tube 114 and liquid tube 112 (seen for example in FIG. 3a). Gas and fluid tubes may be inserted into, and affixed to proximal opening 110 of I/I channels manifold which delivers cleaning fluids to I/I injectors 364 and 366. The gas and liquid tubes (such as gas tube 114 and liquid tube 112) may be threaded through flexible shaft 260 and are used for delivering fluid (gas and/or liquid) to I/I injectors 364 and 366 for cleaning the optical surfaces on the endoscope's tip section and for inflating a body cavity. The gas and liquid tubes (such as gas tube 114 and liquid tube 112) may also be combined into one tube and connected to the tip section as one tube.

It should be realized that it is important to keep the dimensions of the tip section of the endoscope small. Within the tight confines of the endoscope's tip to section are the sensors, lenses, electric cables, at least one working channel, and a plurality of fluid channels. In contrast to endoscopes of the art, wherein each of the fluid tubes was directed to its destination, embodiments of the current invention provide I/I channels manifold to supply cleaning liquid and gas to the plurality of I/I injectors.

While FIG. 2c generically depicts the unitary fluid channeling component 190, and shows its proximal surface 191, the following figures depict some specific exemplary embodiments of the I/I channels manifolds and main bodies (such as cylinders), according to embodiments within the general scope of the current invention.

FIG. 3a schematically depicts a partially disassembled tip section 230a of an endoscope having I/I channels manifold internal to unitary fluid channeling component 190a according to a first exemplary embodiment of the current invention.

Cover 196a is designed to fit over inner part (of the tip section) 100a, and to provide protection to the internal components in the inner part. Holes 164', 340', 344', 242a', 336', 242b', 256b', 252b' and 166b' in cover 196a are aligned with the corresponding components and channel openings 164, 165, 144, 242a, 336, 242b, 256b, 252b and 366b in inner part 100a respectively. Optional groove 370b in cover 196a enable cleaning fluid from I/I injector 366b to arrive, and clean the front surface 252b of side looking camera. Not seen in this view are groove 370a, and holes 256a', 252a' and 166a' in cover 196a which are aligned with the corresponding components and channel openings 256a, 252a and 166a on the other side of inner part 100a respectively.

After fitting and attaching cover 196a over inner part 100a, I/I injectors 364, 366a and 366b may be inserted into the corresponding I/I opening 164, 166a and 166b in unitary fluid channeling component 190a through the corresponding holes 164', 166a' and 166b' in cover 196a. Preferably, I/I injectors 364, 366a and 366b may be removed from I/I opening 164, 166a and 166b for cleaning the endoscope after use. Optionally, I/I injectors 364, 366a and 366b may be replaceable or disposable. Optionally, the nozzles, such as nozzle 348, nozzle 368 or any other nozzle may be inserted into the unitary fluid channeling component, such as unitary fluid channeling components 190 or 190a, within an isolating (e.g., plastic) part into the opening to allows us better electric isolation particularly when the unitary fluid channeling component and the nozzles are made of metal.

In the first exemplary embodiment of the current invention, I/I opening 164, 166a and 166b are connected to proximal opening 110 for gas tube 114 and liquid tube 112 via I/I manifold channels which are within unitary fluid channeling component 190a. Distal opening 344' is the opening of a jet fluid channel which may be used for providing high pressure jet of fluid such as water or saline for cleaning the walls of the body cavity (such as the colon) and optionally for suction.

Figure 3B:
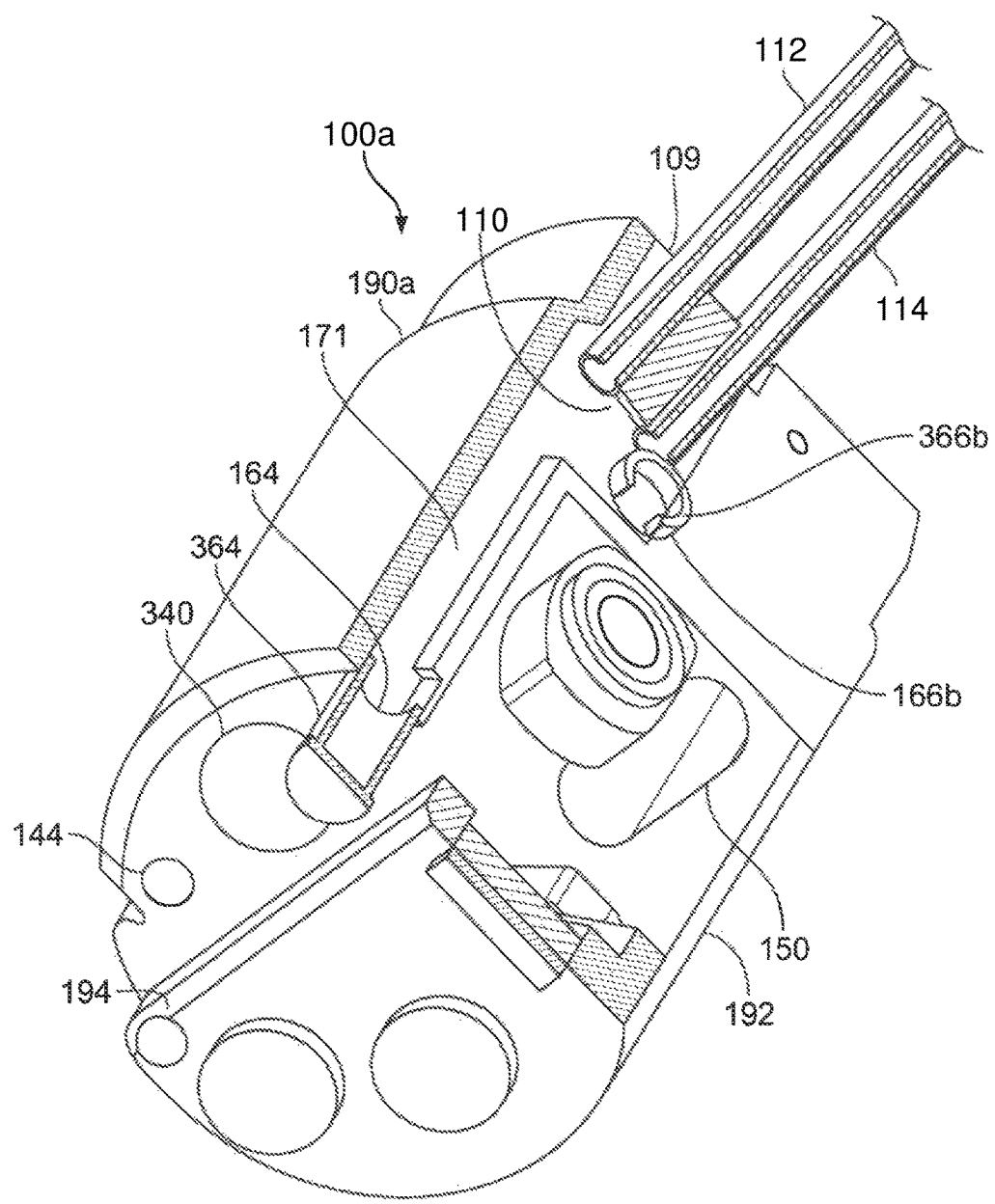
FIG. 3b schematically depicts an isometric cross section of an inner part of a tip section, having I/I channels manifold internal to a unitary fluid channeling component, according to a first exemplary embodiment of the current invention.

FIG. 3b schematically depicts an isometric cross section of Inner part 100a having I/I channels manifold internal to unitary fluid channeling component 190a according to a first exemplary embodiment of the current invention.

In the depicted embodiment gas tube 114 and liquid tube 112 are terminated in a plug 109 adapted to fit into proximal opening 110. It should be noted that although gas tube 112 appears above liquid tube 114, their order may be reversed, they may be positioned side by side, or replaced with a single tube or the tubes may be joined to one tube before entering inner part 100a. Alternatively, each of gas tube 114 and liquid tube 112 is separately connected to unitary fluid channeling component 190, and their lumens open to a common conduit.

Proximal opening 110 for gas tube 114 and liquid tube 112 is opened to I/I channel manifold. This cross section shows proximal opening 110 opened to front I/I channel 171 leading to front I/I opening 164 into which front I/I injector 364 is inserted. According to some embodiments, front I/I channel 171 (may also be referred to as front fluid channel) may be drilled in unitary fluid channeling component 190a. It should be noted that unitary fluid channeling component 190a and other parts of inner part 100a may be machined or be made by casting, sintering, injection or other manufacturing techniques.

Figure 3C:
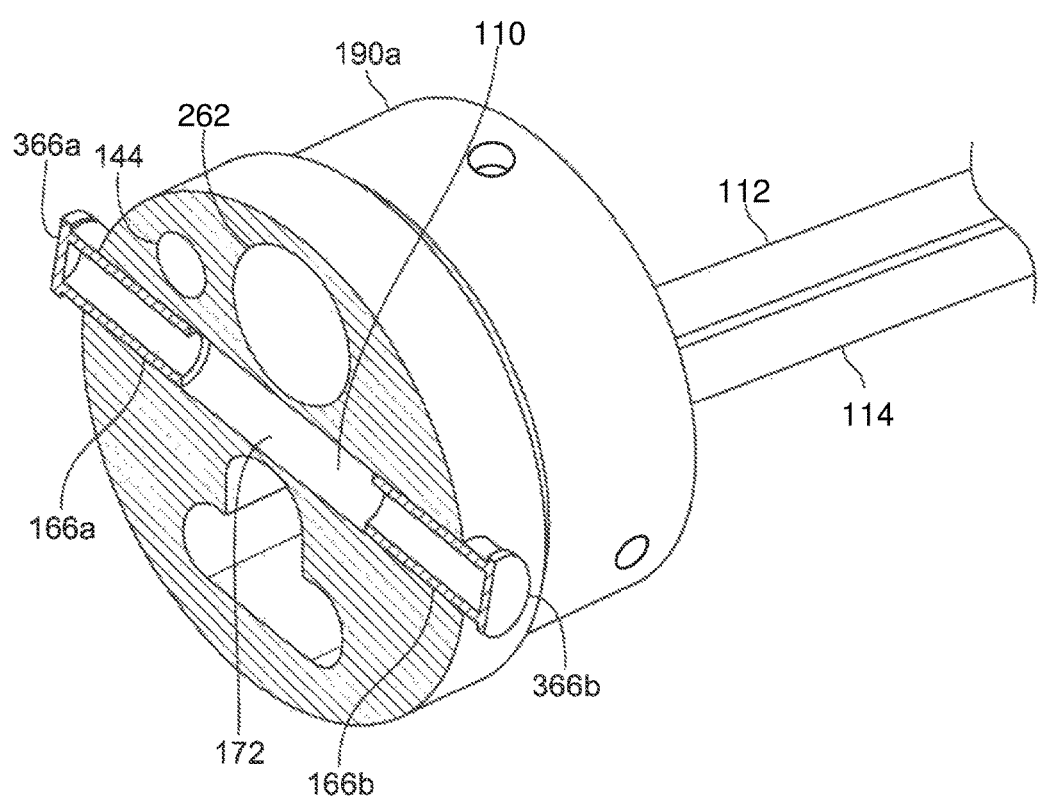
FIG. 3c schematically depicts an isometric cross section of a unitary fluid channeling component of an inner part of a tip section having I/I channels manifold internal to the unitary fluid channeling component, according to a first exemplary embodiment of the current invention.
Figure 3D:
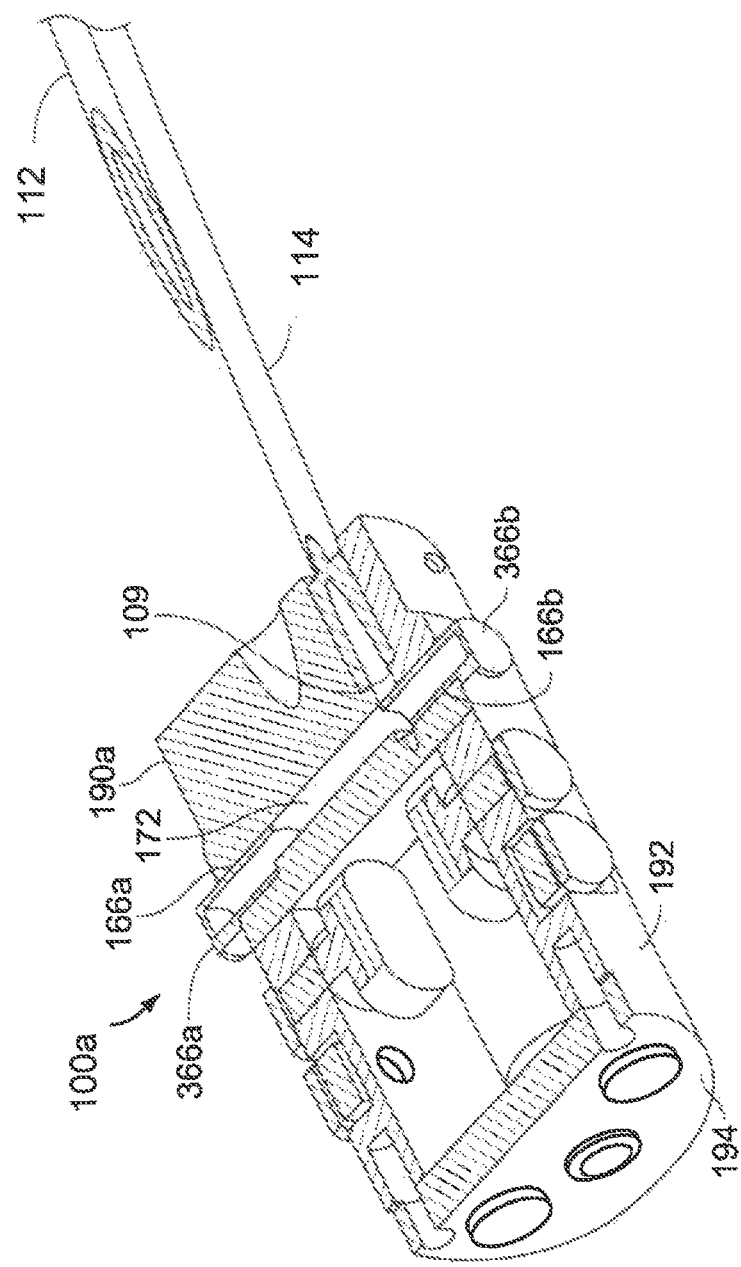
FIG. 3d schematically depicts another isometric cross section of an inner part of a tip section, showing the unitary fluid channeling component having I/I channels manifold internal to it, according to a first exemplary embodiment of the current invention.

Reference is now made to FIG. 3c, which schematically depicts an isometric cross section of unitary fluid channeling component 190a having I/I channels manifold internal to it according to a first exemplary embodiment of the current invention and to FIG. 3d, which schematically depicts another isometric cross section of inner part 110a, showing unitary fluid channeling component 190a having I/I channels manifold internal to it according to a first exemplary embodiment of the current invention.

Proximal opening 110 for gas tube 114 and liquid tube 112 is seen in this figure opened to I/I channel manifold. This cross section shows proximal opening 110 opened to cross I/I channel 172 (may also be referred to as side fluid channel or side I/I channel) leading to left I/I opening 166a into which left I/I injector 366a is inserted and to right I/I opening 166b into which right I/I injector 366b is inserted.

According to some embodiments, cross I/I channel 172 may be drilled in unitary fluid channeling component 190a.

According to the first exemplary embodiment of the current invention, proximal opening 110 for gas tube 114 and liquid tube 112 is directly opened to I/I channel manifold, within unitary fluid channeling component 190a which comprises:

a) a right I/I opening 166b, connected to proximal opening 110, and into which right I/I injector 366b is inserted;

b) a front I/I channel 171 connected to proximal opening 110, and leading to front I/I opening 164 into which front I/I injector 364 is inserted; and c) a cross I/I channel 172, connected to the proximal opening, and which is opened to left I/I opening 166a into which left I/I injector 366a is inserted.

Figure 4A:
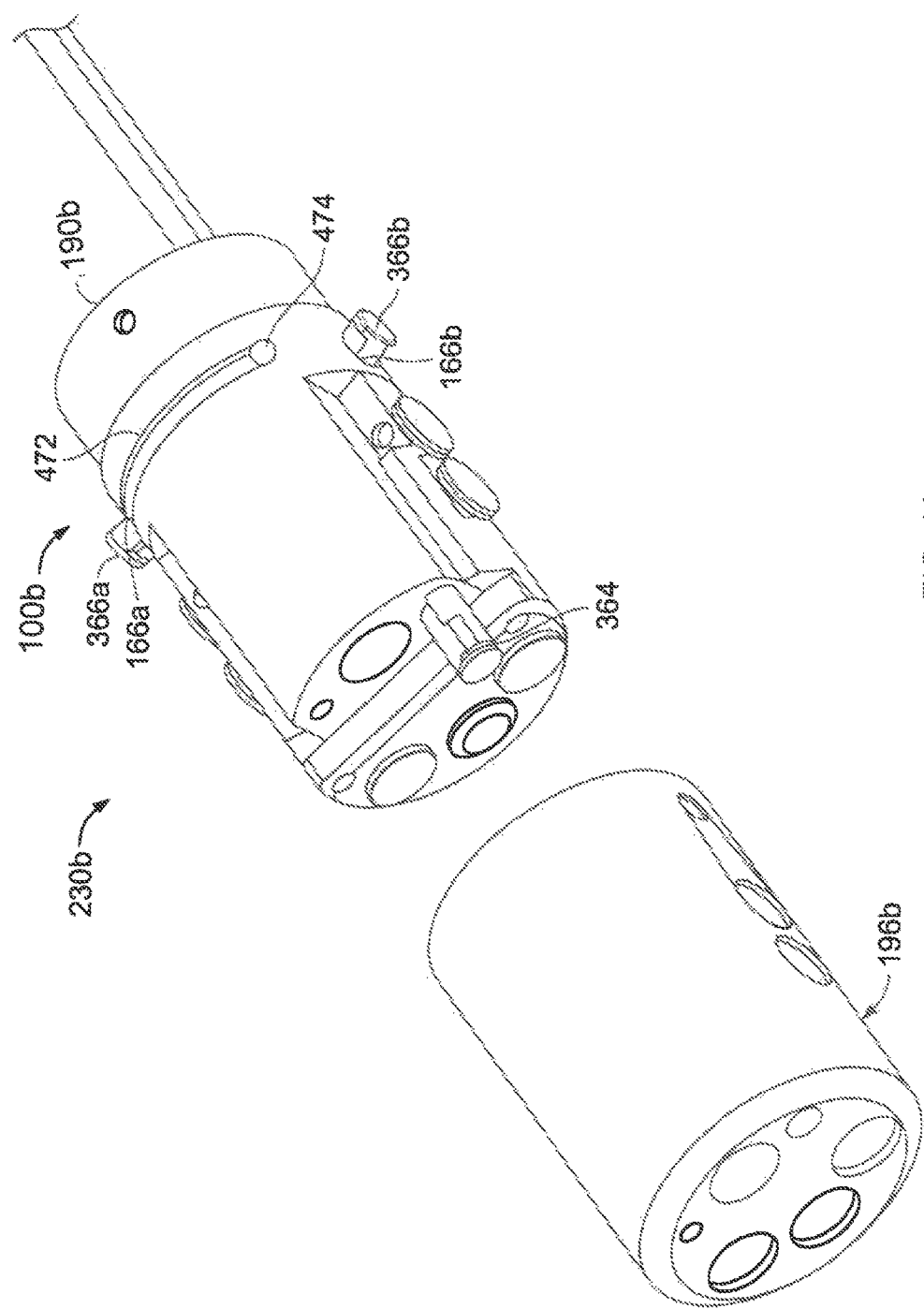
FIG. 4a schematically depicts an isometric view of a partially disassembled tip section of an endoscope having I/I channels manifold partially internal and partially external to the unitary fluid channeling component of the tip section, according to a second exemplary embodiment of the current invention.

FIG. 4a schematically depicts an isometric view of a partially disassembled tip section 230b of an endoscope having I/I channels manifold partially internal and partially external to unitary fluid channeling component 190b according to a second exemplary embodiment of the current invention.

In contrast to the first embodiment depicted in FIG. 3, in the embodiment depicted in FIG. 4, cleaning fluids are supplied to left I/I injector 366a via a groove 472 in unitary fluid channeling component 190b. Groove 472 is connected in one side to proximal opening 110 by hole 474 and is opened to left I/I opening 166a which can hardly be seen in this view.

Cover 196b is designed to fit over inner part 100b, and to provide protection to the internal components of inner part 100b. Additionally, cover 196b is tightly fitted and preferably hermetically seals groove 472 to convert it to fluid tight conduit.

Figure 4B:
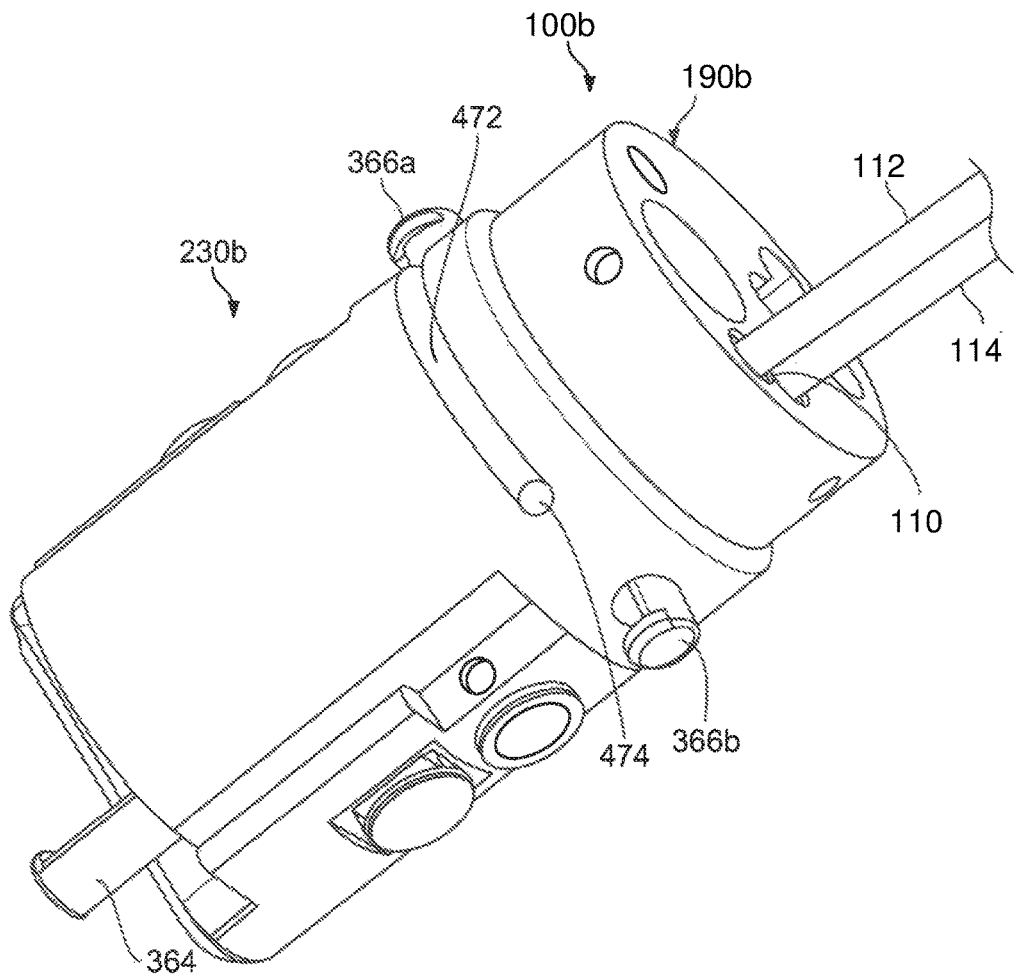
FIG. 4b schematically depicts an isometric view of an inner part of a tip section having I/I channels manifold partially internal and partially external to the unitary fluid channeling component of the tip section, according to a second exemplary embodiment of the current invention.

FIG. 4b schematically depicts an isometric view of inner part 100b of an endoscope tip section having I/I channels manifold partially internal and partially external to unitary fluid channeling component 190b according to a second exemplary embodiment of the current invention.

Figure 4C:
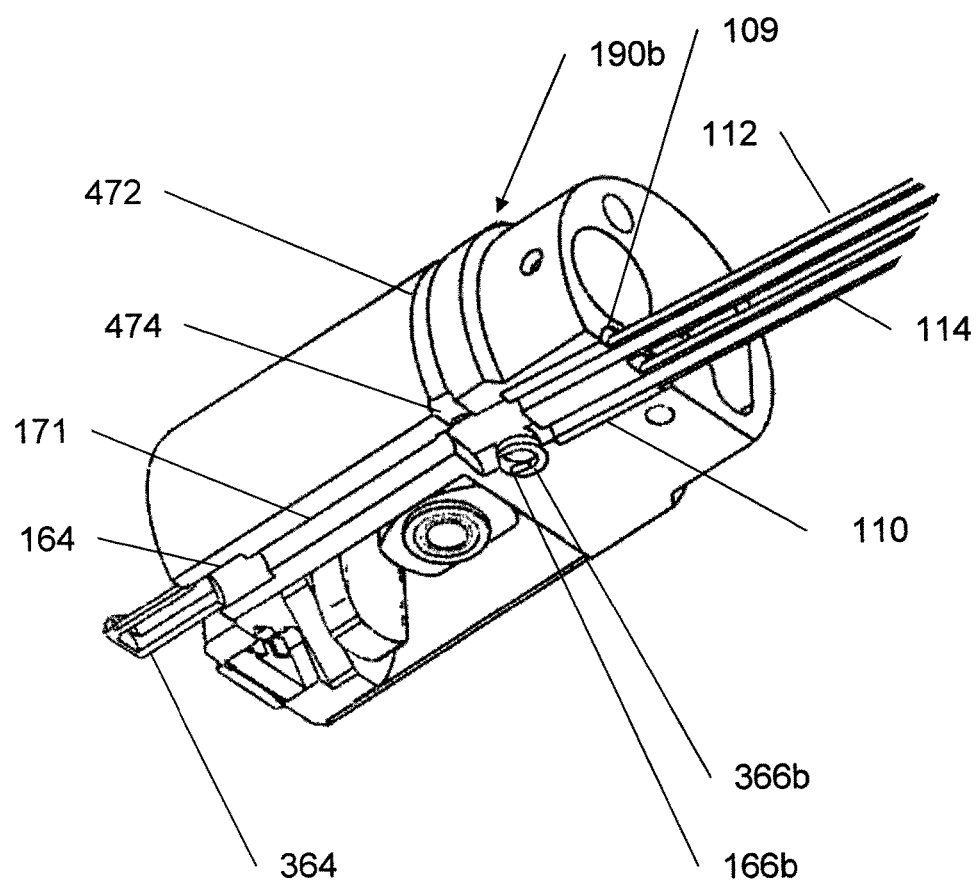
FIG. 4c schematically depicts an isometric cross section of the inner part, according to the second exemplary embodiment of the current invention.

FIG. 4c schematically depicts an isometric cross section of unitary fluid channeling component 190b according to the second exemplary embodiment of the current invention.

According to the second exemplary embodiment of the current invention, proximal opening 110 for gas tube 114 and liquid tube 112 is seen in this figure opened to I/I channel manifold which comprises:

a) a right I/I opening 166b, connected to proximal opening 110, into which right I/I injector 366b is inserted;

b) a front I/I channel 171 connected to front I/I opening 164 into which front I/I injector 364 is inserted; and c) hole 474 connected to groove 472 which is opened to left I/I opening 166a (not seen here) into which left I/I injector 366a (not seen here) is inserted.

Figure 5A:
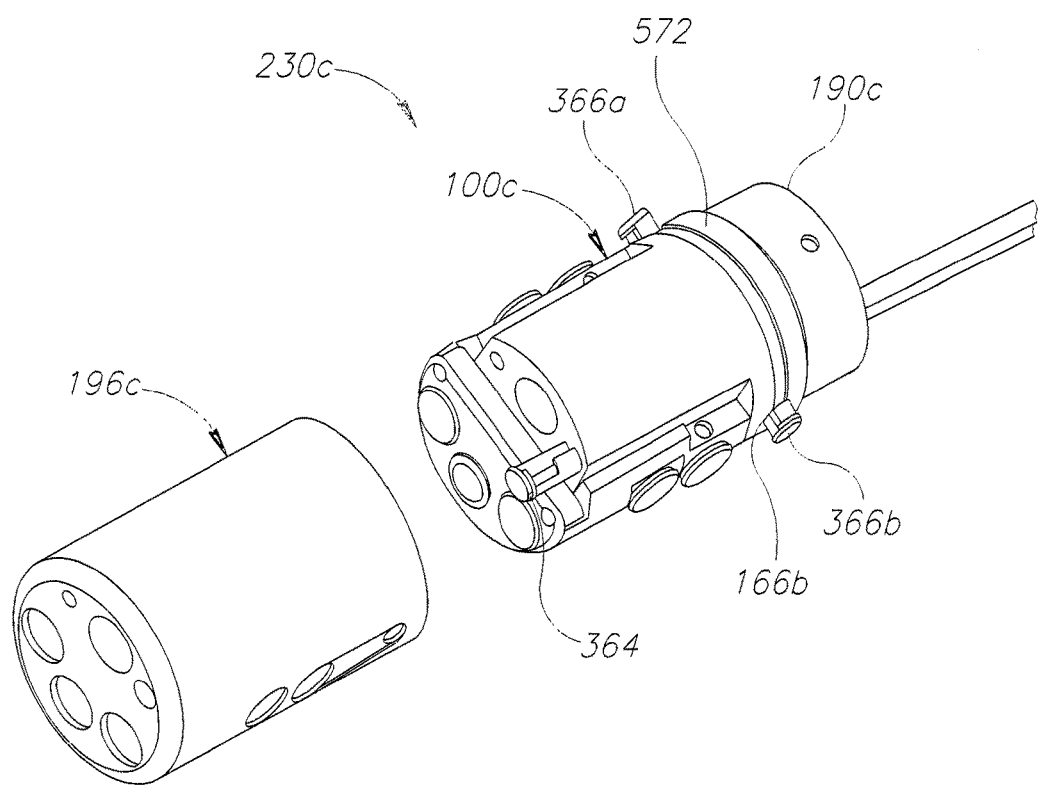
FIG. 5a schematically depicts an isometric view of a partially disassembled tip section of an endoscope having I/I channels manifold partially internal and partially external to the unitary fluid channeling component of the tip section, according to a third exemplary embodiment of the current invention.

FIG. 5a schematically depicts an isometric view of a partially disassembled tip section 230c of an endoscope having I/I channels manifold partially internal and partially external to unitary fluid channeling component 190c according to a third exemplary embodiment of the current invention.

In contrast to the first embodiment depicted in FIG. 3, in the embodiment depicted in FIG. 5, fluids (liquid and/or gas) are supplied to left I/I injector 366b via a groove 572 in unitary fluid channeling component 190c. However, in contrast to the second embodiment, depicted in FIG. 4, groove 572 is connected in the right side to right I/I opening 166b and opened on the left to left I/I opening 166a which can hardly be seen in this view.

Cover 196c is designed to fit over inner part 100c, and to provide protection to the internal components of inner part 100c. Additionally, cover 196c is tightly fitted and preferably hermetically seals groove 572 to convert it to fluid tight conduit.

Figure 5B:
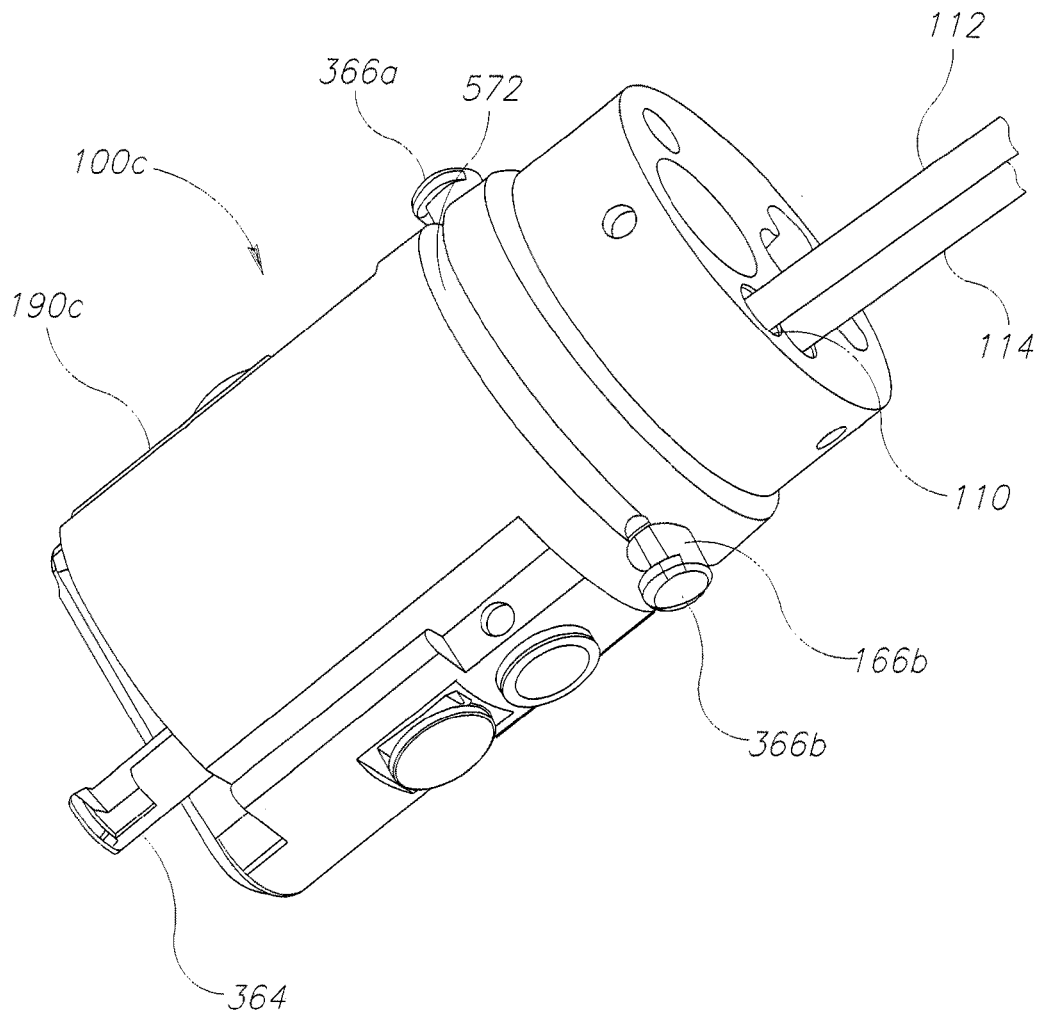
FIG. 5b schematically depicts an isometric view of an inner part of a tip section having I/I channels manifold partially internal and partially external to a unitary fluid channeling component of the inner part of the tip section, according to a third exemplary embodiment of the current invention.

FIG. 5b schematically depicts an isometric view of inner part 100c of an endoscope tip section having I/I channels manifold partially internal and partially external to unitary fluid channeling component 190c according to a third exemplary embodiment of the current invention.

It should be noted that the location of groove 572 on surface of unitary fluid channeling component 190c, and its depth and shape may be different.

Figure 5C:
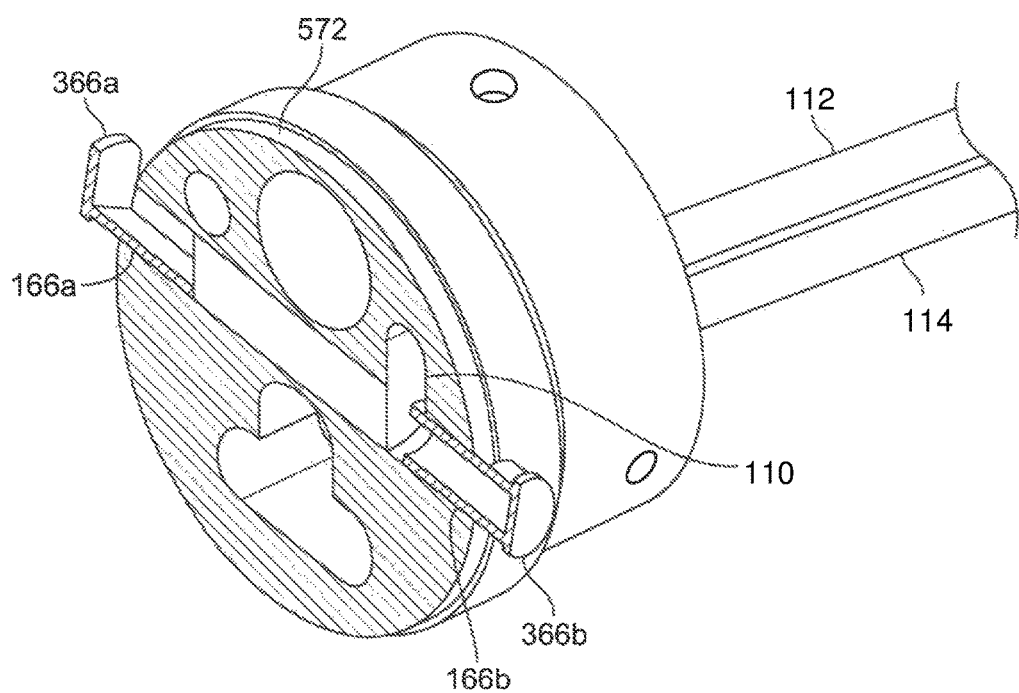
FIG. 5c schematically depicts an isometric cross section of the unitary fluid channeling component, according to the third exemplary embodiment of the current invention.

FIG. 5c schematically depicts an isometric cross section of unitary fluid channeling component 190c according to the third exemplary embodiment of the current invention.

Proximal opening 110 for gas tube 114 and liquid tube 112 is seen in this figure opened to right I/I opening 166b and through it to groove 572 leading to left I/I opening 166a.

Figure 5D:
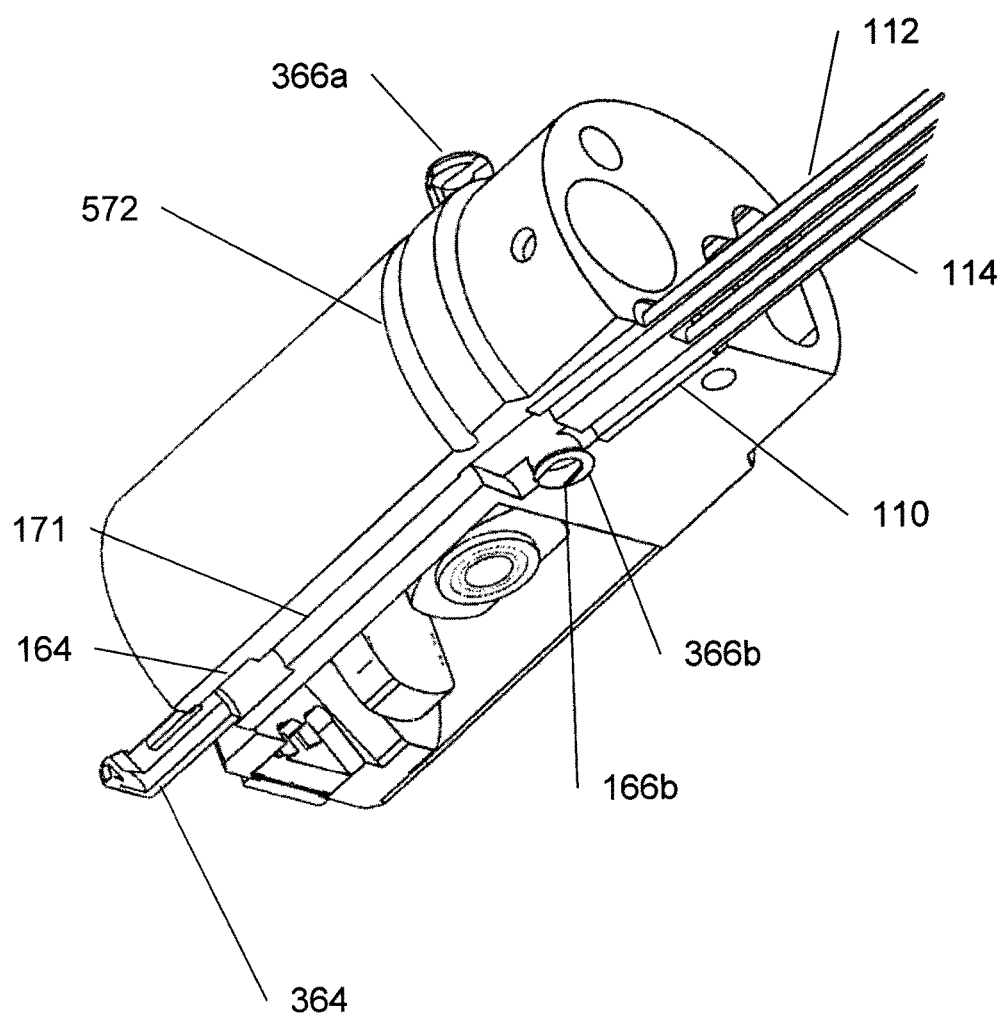
FIG. 5d schematically depicts another isometric cross section of an inner part of a tip section of an endoscope, according to the third exemplary embodiment of the current invention.

FIG. 5d schematically depicts another isometric cross section of unitary fluid channeling component 190c according to the third exemplary embodiment of the current invention.

Proximal opening 110 for gas tube 114 and liquid tube 112 is seen in this figure opened to right I/I opening 166b and through it to I/I manifold which comprises:

a) a right I/I opening 166b, connected to proximal opening 110, into which right I/I injector 366b is inserted;

b) a front I/I channel 171, connected to proximal opening 110, ad leading to front I/I opening 164 into which front I/I injector 364b is inserted; and c) a groove 572 which receives cleaning fluids from right I/I opening 166b, and is opened to left I/I opening 166a (not seen here) into which left I/I injector 366a is inserted.

Figure 6A:
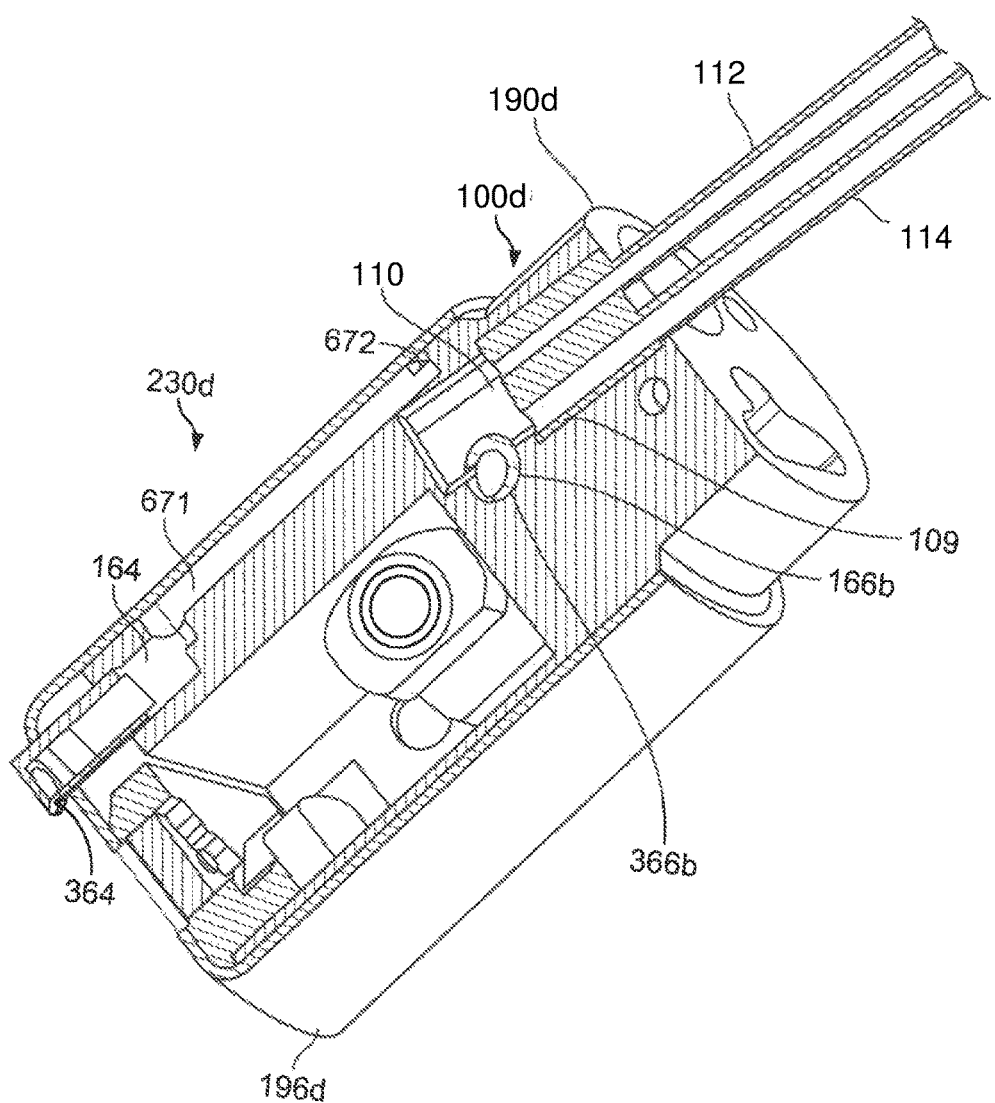
FIG. 6a schematically depicts an isometric cross section view of an assembled tip section of an endoscope having I/I channels manifold external to a unitary fluid channeling component of the inner part of the tip section, according to a forth exemplary embodiment of the current invention.

FIG. 6a schematically depicts an isometric cross section view of an assembled tip section 230d of an endoscope having I/I channels manifold external to unitary fluid channeling component 190d according to a forth exemplary embodiment of the current invention.

Similarly to third embodiment depicted in FIG. 5, groove 672 is connected in the right side to right I/I opening 166b and opened on the left to left I/I opening 166a.

However in contrast to the first, second and third embodiments depicted in FIGS. 3, 4, and 5, in the embodiment depicted in FIG. 6, fluids are supplied to front I/I injector 364 via a front groove 671 in unitary fluid channeling component 190d. Front groove 671 is opened in its proximal end to groove 672, and at its distal end to front I/I opening 164.

Cover 196d is designed to fit over inner part 100d, and to provide protection to the internal components of inner part 100d. Additionally, cover 196d is tightly fitted and preferably hermetically seals grooves 671 and 672 to convert them to fluid tight conduits.

Figure 6B:
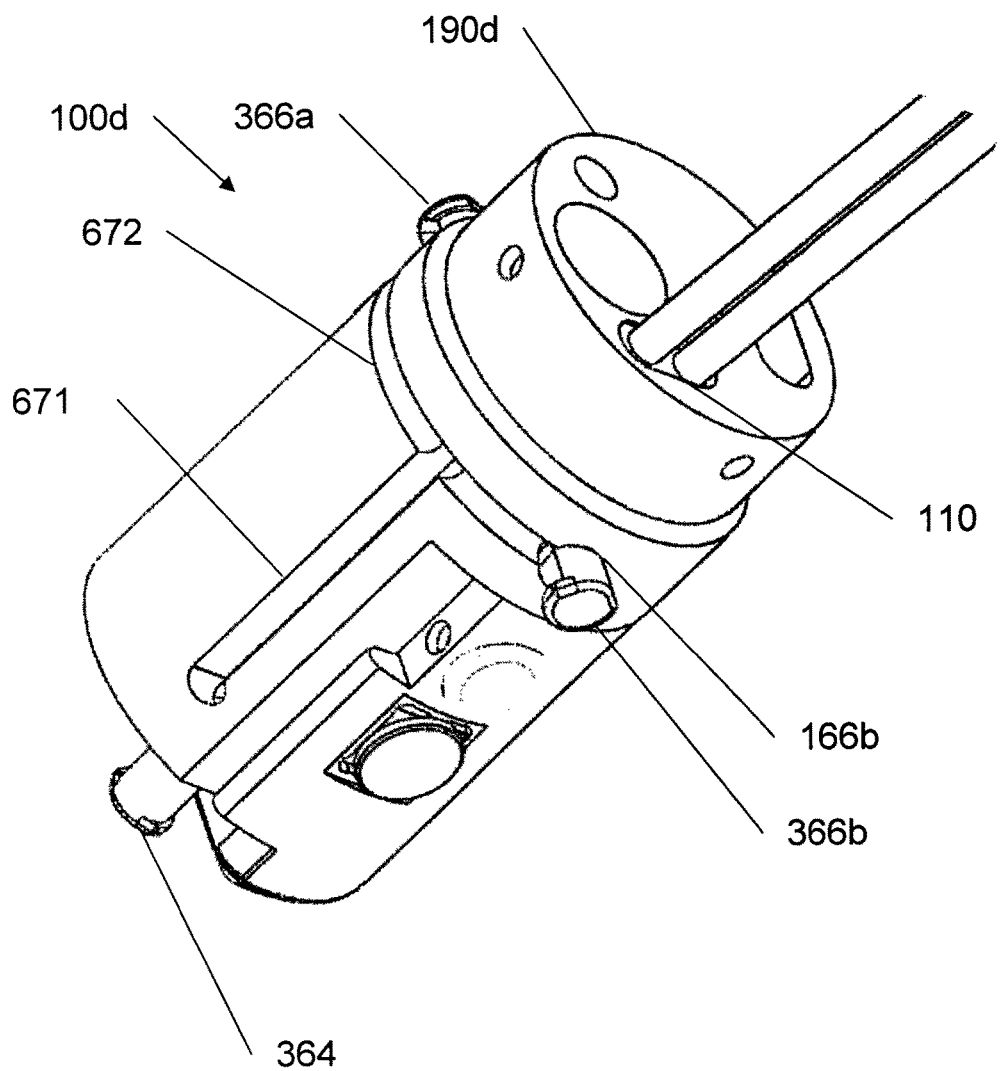
FIG. 6b schematically depicts an isometric view of an inner part of a tip section having I/I channels manifold external to the unitary fluid channeling component, according to the forth exemplary embodiment of the current invention.

FIG. 6b schematically depicts an isometric view of inner part 100d of an endoscope tip section having I/I channels manifold external to unitary fluid is channeling component 190d according to a forth exemplary embodiment of the current invention.

It should be noted that the location of grooves 671 and 672 on surface of unitary fluid channeling component 190d, and their depth and shape may be different. For example, the location of any of the grooves may be completely or partially inside the cover, for example, within the walls of the cover.

Figure 6C:
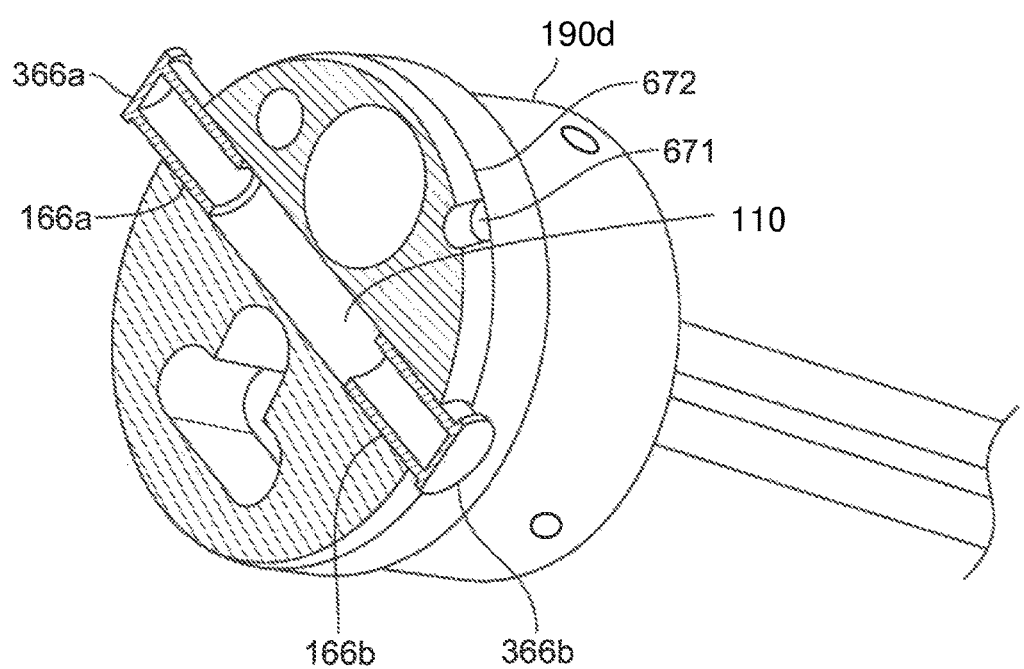
FIG. 6c schematically depicts an isometric cross section of a unitary fluid channeling component, according to the forth exemplary embodiment of the current invention.

FIG. 6c schematically depicts an isometric cross section of unitary fluid channeling component 190d according to the forth exemplary embodiment of the current invention.

Proximal opening 110 for gas tube 114 and liquid tube 112 is seen in this figure opened to right I/I opening 166b and through it to groove 672 leading to left I/I opening 166a. Also seen in this figure is the intersection of grooves 672 and front groove 671

According to the forth embodiment of the current invention, proximal opening 110 for gas tube 114 and liquid tube 112 is opened to right I/I opening 166b and through it to an I/I manifold which comprises:

a) a right I/I opening 166b, connected to proximal opening 110, into which right I/I injector 366b is inserted;

b) groove 672 which receives cleaning fluids from right I/I opening 166b, and is opened to left I/I opening 166a into which left I/I injector 366a is inserted; and c) front I/I groove 671, receiving I/I fluids from groove 672, and connected to front I/I opening 164 into which front I/I injector 364 is inserted.

Figure 7A:
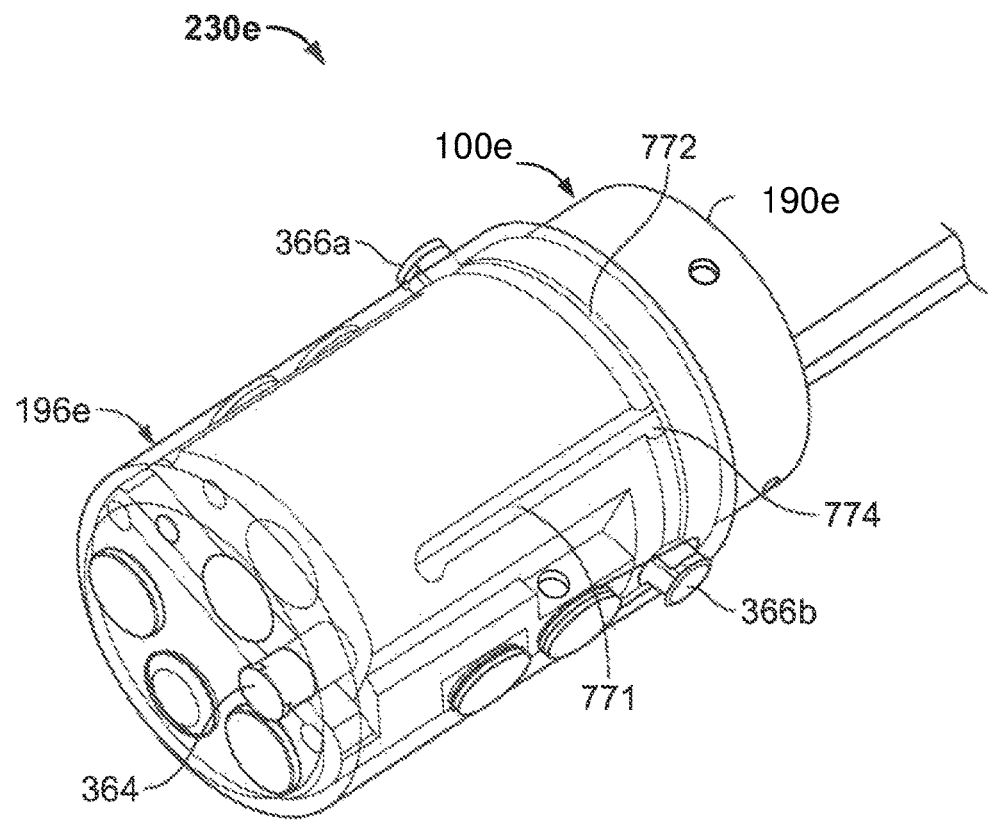
FIG. 7a schematically depicts an isometric view of an assembled tip section of an endoscope having I/I channels manifold partially external to a unitary fluid channeling component of an inner part of the tip section, according to a fifth exemplary embodiment of the current invention.

FIG. 7a schematically depicts an isometric view of an assembled tip section 230e of an endoscope having I/I channels manifold partially external to unitary fluid channeling component 190e according to a fifth exemplary embodiment of the current invention.

For clarity, cover 196d was drawn partially transparent to show inner part 100e.

Similarly to second embodiment depicted in FIG. 4, groove 772 is proximal opening 110 by hole 774 and opened on the left to left I/I opening 166a (not seen in this figure).

Similarly to the forth embodiment depicted in FIG. 5, cleaning fluids are supplied to front I/I injector 364 via a front groove 771 in unitary fluid channeling component 190e. Front groove 771 is opened in its proximal end to groove 772, and at its distal end to front I/I opening 164.

Cover 196e is designed to fit over inner part 100e, and to provide protection to the internal components of inner part 100e. Additionally, cover 196e is tightly fitted and preferably hermetically seals grooves 771 and 772 to convert them to fluid tight conduits.

Figure 7B:
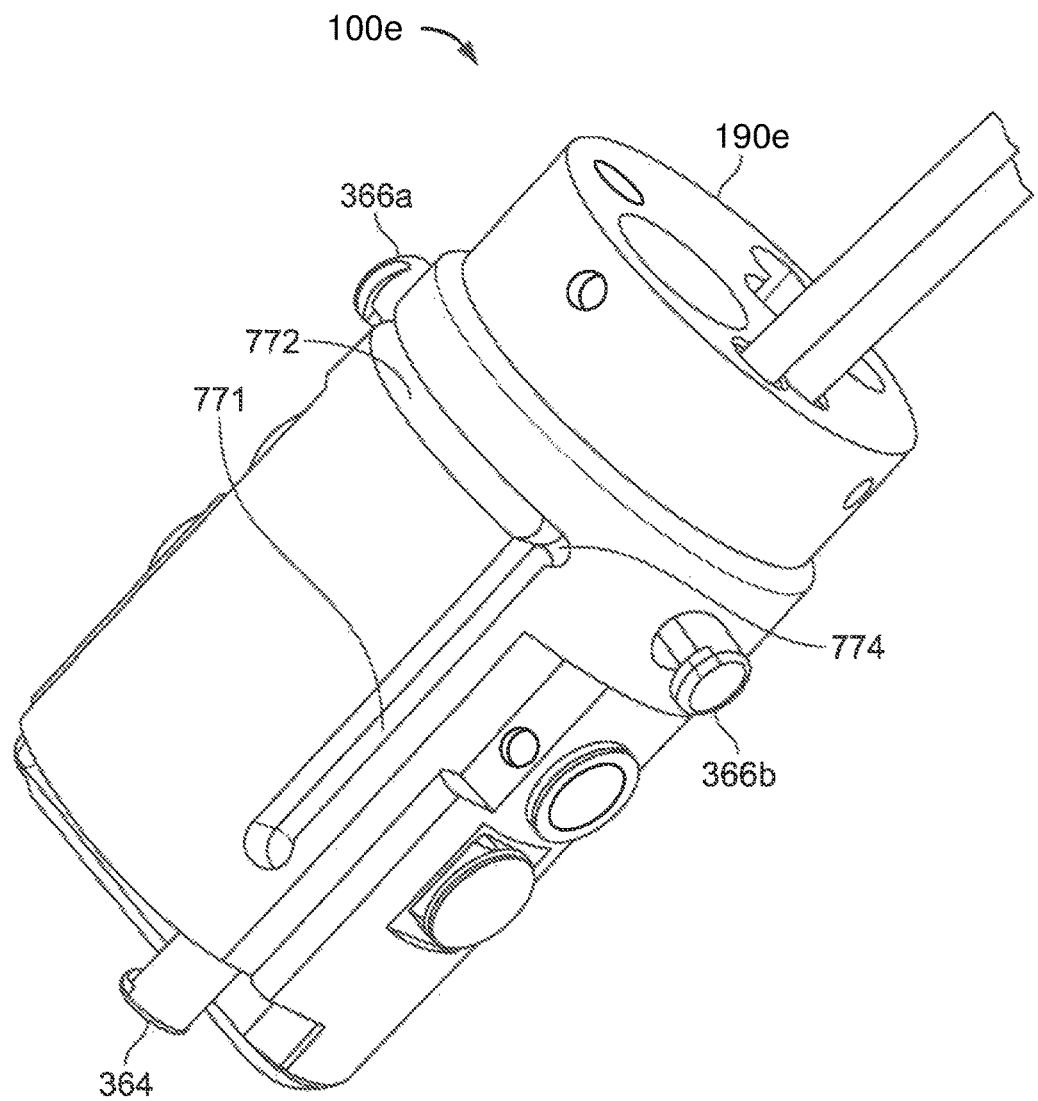
FIG. 7b schematically depicts an isometric view of an inner part of a tip is section having I/I channels manifold partially external to the unitary fluid channeling component, according to the fifth exemplary embodiment of the current invention.

FIG. 7b schematically depicts an isometric view of inner part 100e of an endoscope tip section having I/I channels manifold partially external to unitary fluid channeling component 190e according to a fifth exemplary embodiment of the current invention.

It should be noted that the location of grooves 771 and 772 on surface of unitary fluid channeling component 190d, and their depth and shape may be different.

Figure 7C:
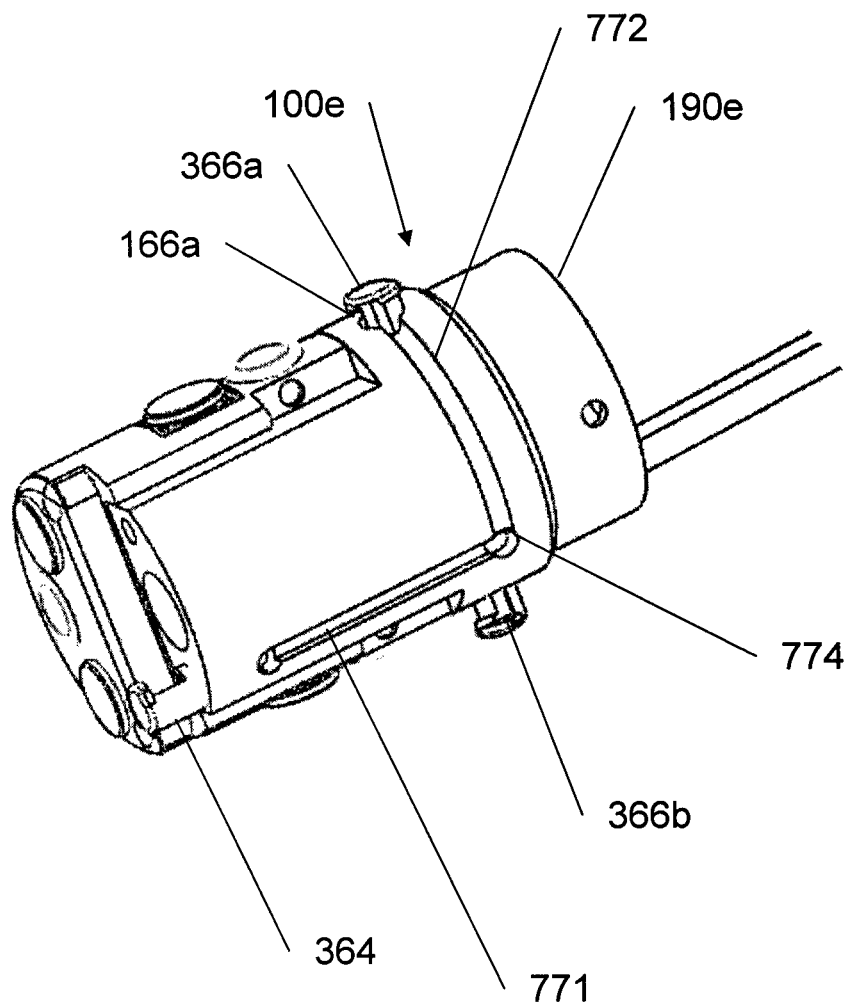
FIG. 7c schematically depicts another isometric view of an inner part of a tip section having I/I channels manifold partially external to the unitary fluid channeling component, according to a fifth exemplary embodiment of the current invention.

FIG. 7c schematically depicts another isometric view of inner part 100e of an endoscope tip section having I/I channels manifold partially external to unitary fluid channeling component 190e according to a fifth exemplary embodiment of the current invention.

This view depicts groove 772 connection to left I/I opening 166a.

Figure 7D:
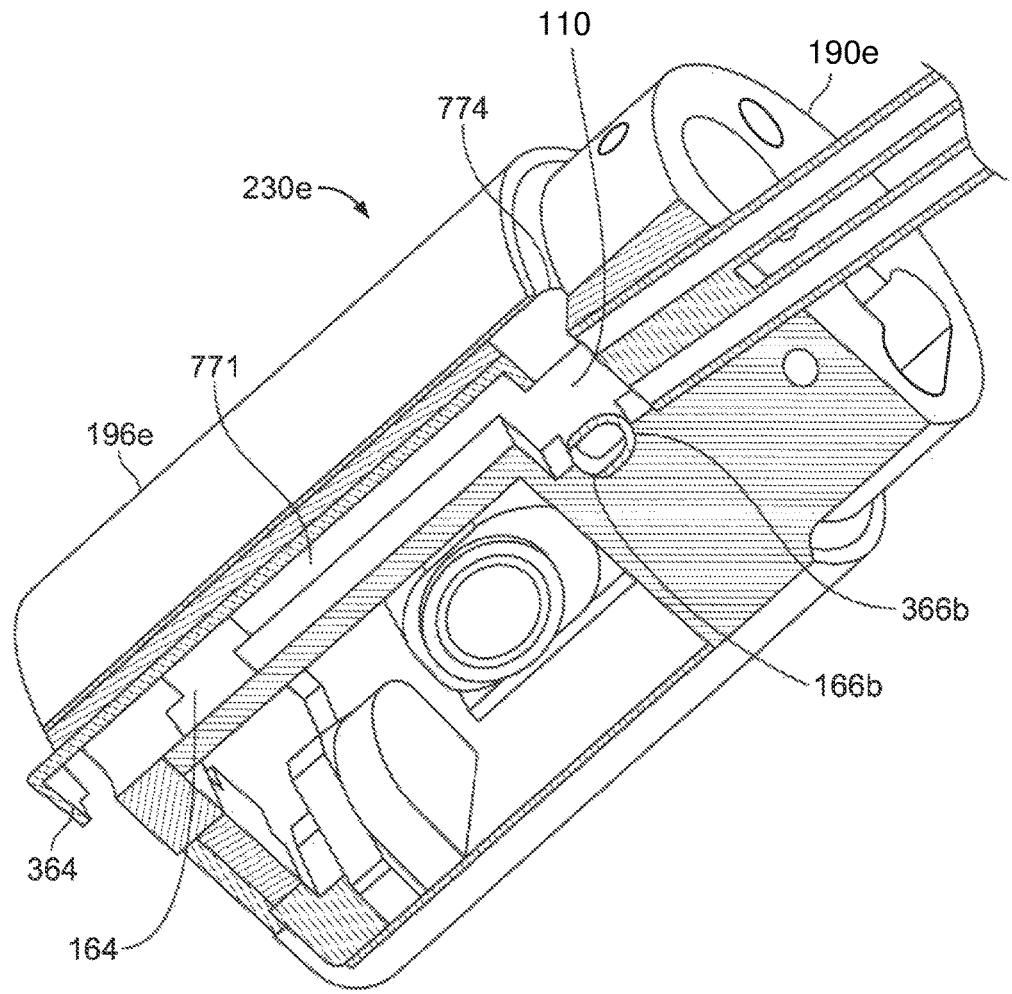
FIG. 7d schematically depicts an isometric cross section of an endoscope tip section according to the fifth exemplary embodiment of the current invention.

FIG. 7d schematically depicts an isometric cross section of endoscope tip section 230e according to the fifth exemplary embodiment of the current invention.

Proximal opening 110 for gas tube 114 and liquid tube 112 is seen in this figure opened to right I/I opening 166b. Also seen in this figure is hole 774 connecting proximal opening 110 to front groove 771 and the connection of front groove 771 to front get opening 164.

According to the fifth embodiment of the current invention, proximal opening 110 for gas tube 114 and liquid tube 112 is opened to right I/I opening 166b and through hole 774 to I/I manifold which comprises:

a) a right I/I opening 166b, connected to proximal opening 110, into which right I/I injector 366b is inserted;

b) groove 772 which receives fluids via hole 774 connected to proximal opening 110, and is opened to left I/I opening 166a into which left I/I injector 366a is inserted; and c) front I/I groove 771, receiving I/I fluids from hole 774, and connected to front I/I opening 164 into which front I/I injector 364b is inserted.

Figure 8A:
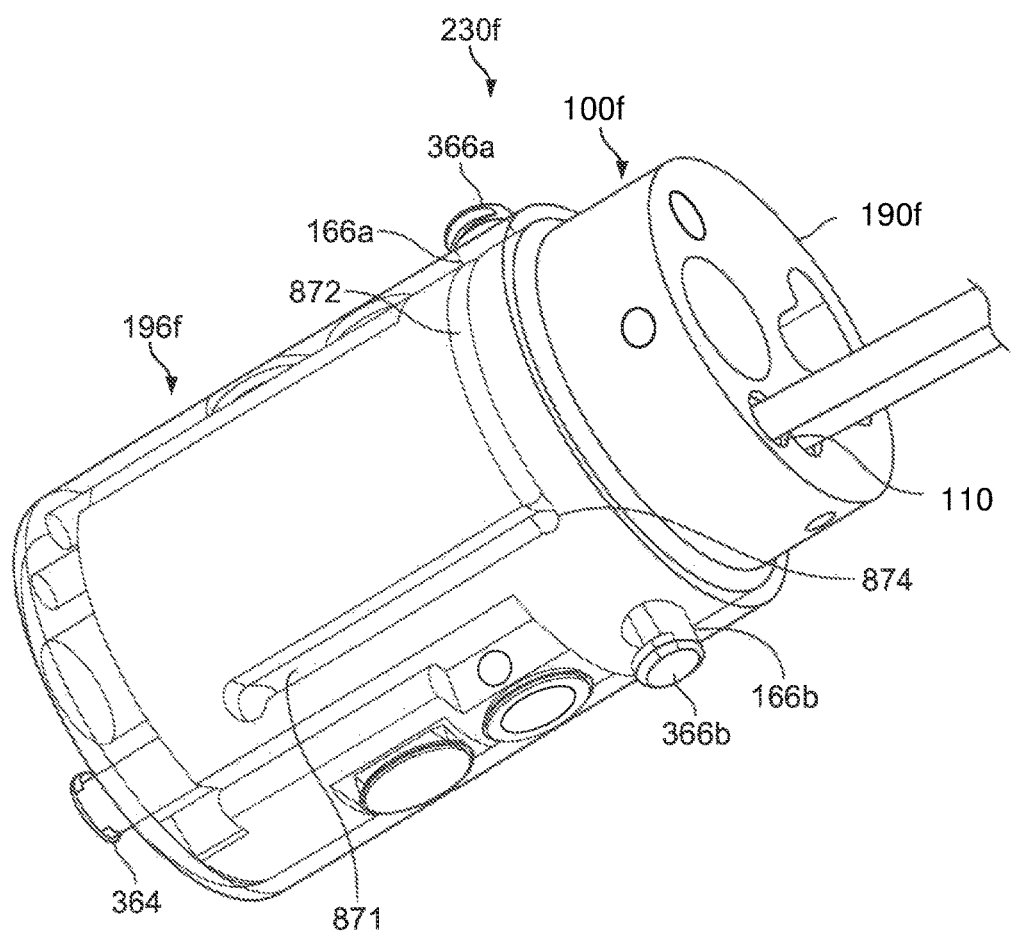
FIG. 8a schematically depicts an isometric view of an assembled tip section of an endoscope having I/I channels manifold external to a unitary fluid channeling component of an inner part of the tip section, according to a sixth exemplary embodiment of the current invention.

FIG. 8a schematically depicts an isometric view of an assembled tip section 230f of an endoscope having I/I channels manifold external to unitary fluid channeling component 190f in inner part 100f according to a sixth exemplary embodiment of the current invention.

Similarly to forth embodiment depicted in FIG. 6, groove 872 in unitary fluid channeling component 190f is connected in the right side to right I/I opening 166b and opened on the left to left I/I opening 166a.

Similarly to forth embodiment depicted in FIG. 6, front groove 871 is connected in its proximal end to groove 872.

However in contrast to the forth embodiment cleaning fluids are supplied groove 871 and 872 via hole 874 connecting them to proximal opening 110.

Cover 196f is designed to fit over inner part 100f, and to provide protection to the internal components of inner part 100f. Additionally, cover 196f is tightly fitted and preferably hermetically seals grooves 871 and 872 to convert them to fluid tight conduits.

Figure 8B:
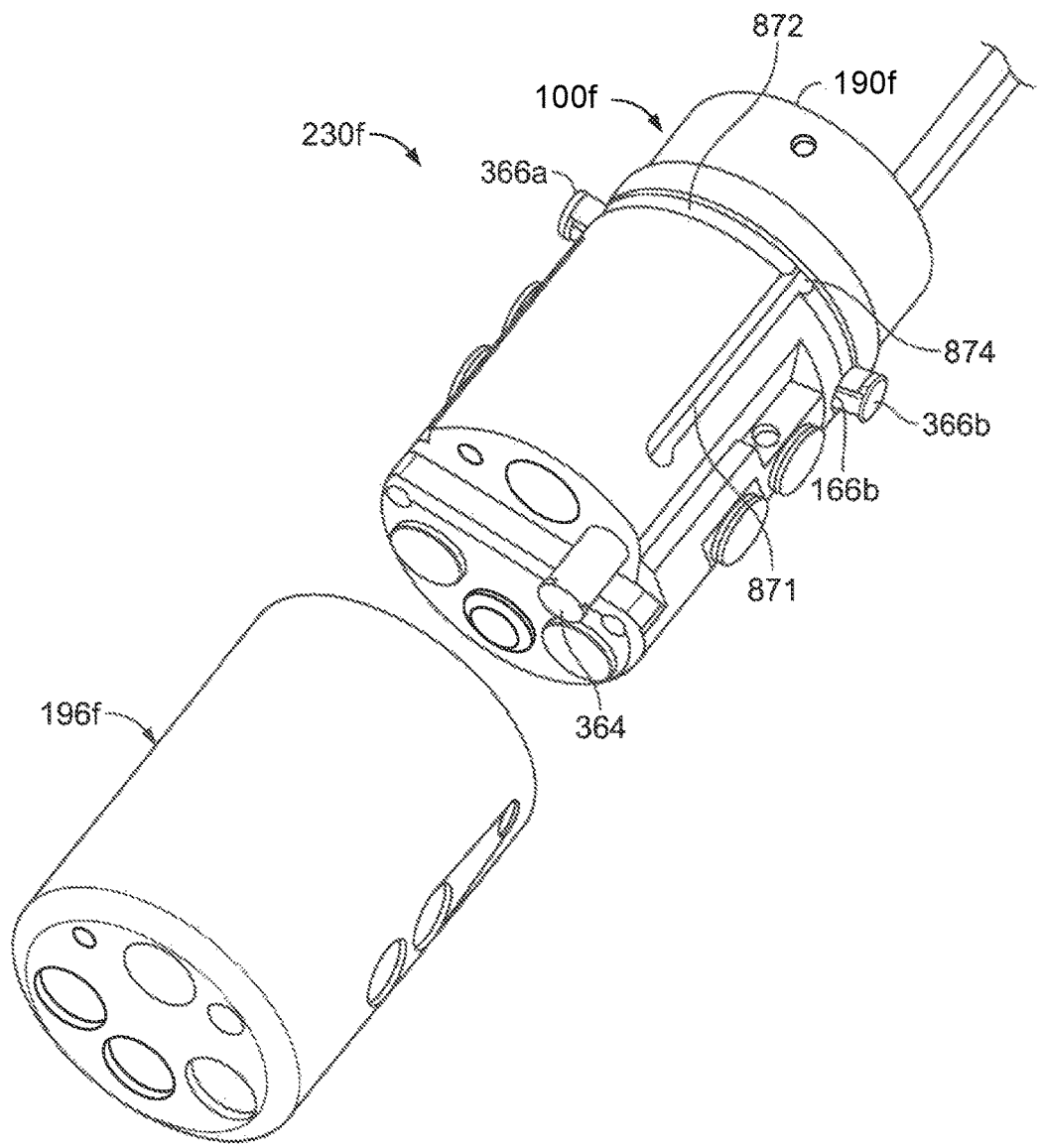
FIG. 8b schematically depicts an isometric view of a partially disassembled tip section of an endoscope having I/I channels manifold external to the unitary fluid channeling component, according to a sixth exemplary embodiment of the current invention.

FIG. 8b schematically depicts an isometric view of a partially disassembled tip section 230f of an endoscope having I/I channels manifold external to unitary fluid channeling component 190f in inner part 100f according to a sixth exemplary embodiment of the current invention.

It should be noted that the location of grooves 871 and 872 on surface of unitary fluid channeling component 190d, and their depth and shape may be different.

According to the sixth embodiment of the current invention, proximal opening 110 for gas tube 114 and liquid tube 112 is opened hole 874 and through it to an I/I manifold which comprises:

a) grove 872 which receives cleaning fluids from proximal opening 110 via hole 874; connected to right I/I opening 166b into which right I/I injector 366b is inserted;

b) same groove 872 connected to left I/I opening, to which left I/I injector 366a is inserted; and c) front I/I groove 871, receiving I/I fluids from groove 872, and connected to front I/I opening into which front I/I injector 364 is inserted.

It should be noted that optionally I/I injectors 336a and 336b, and optionally also 364 may be constructed as identical interchangeable inserts.

Figure 9A:
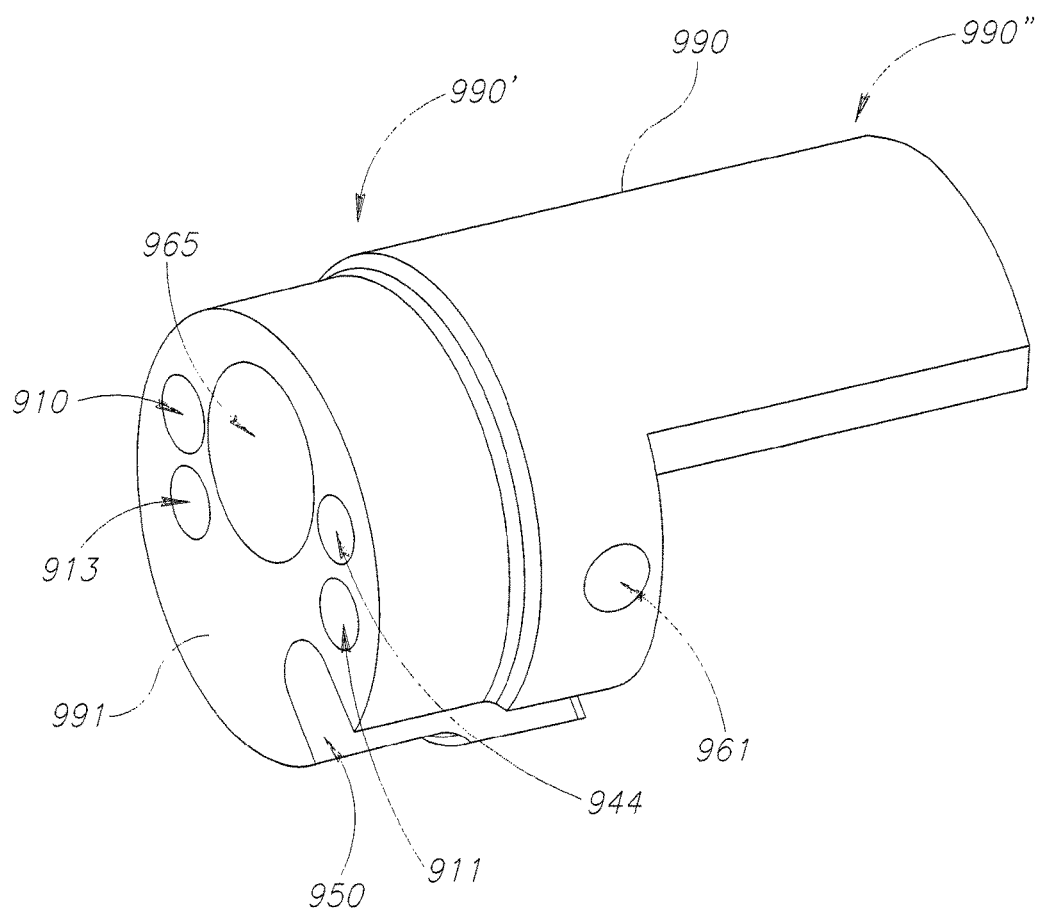
FIG. 9a schematically depicts an isometric proximal view of a main section of an inner part of an endoscope tip section, according to an exemplary embodiment of the current invention.
Figure 9B:
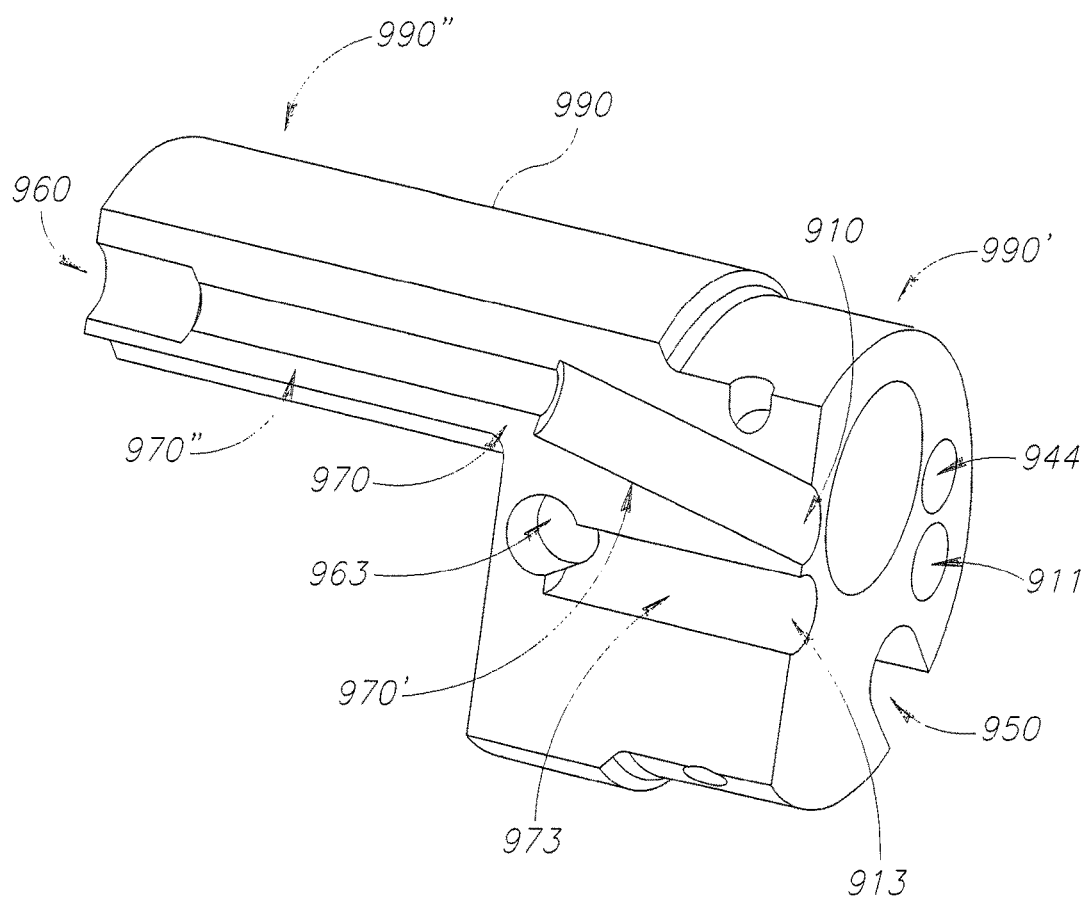
FIG. 9b schematically depicts an isometric cross section of the main section of FIG. 9a, according to an exemplary embodiment of the current invention.

Reference is now made to FIG. 9a which schematically depicts an isometric proximal view of a main section of an inner part of an endoscope tip section, according to an exemplary embodiment of the current invention and to FIG. 9b, which schematically depicts an isometric cross section of the main section of FIG. 9a, according to an exemplary embodiment of the current is invention.

Unitary fluid channeling component 990 of an inner part of a tip section of an endoscope (such as colonoscope) is configured to be located within the tip section and may be used for accommodating fluid channels, work channel and optionally cable channel/recess and for holding in place the components such as tubing/tubes, and injectors. Unitary fluid channeling component 990 may be a part of the inner part of the tip section in a similar manner to that described for example in FIG. 2c.

Unitary fluid channeling component 990, according to some embodiments, may generally include two parts: a proximal fluid channeling component section 990' and a distal fluid channeling component section 990". Proximal fluid channeling component section 990' may have an essentially cylindrical shape. Distal fluid channeling component section 990" may partially continue the cylindrical shape of proximal fluid channeling component section 990' and may have a shape of a partial cylinder (optionally elongated partial cylinder), having only a fraction of the cylinder (along the height axis of the cylinder), wherein another fraction of the cylinder (along the height axis of the cylinder) is missing. Distal fluid channeling component section 990" may be integrally formed as a unitary block with proximal fluid channeling component section 990'. The height of distal fluid channeling component section 990" may by higher than that of proximal fluid channeling component section 990'. In the case of distal fluid channeling component section 990", the shape of the partial cylinder (for example, partial cylinder having only a fraction of a cylinder shape along one side of the height axis) may provide a space to accommodate a central section (not shown).

On proximal surface 991 of fluid channeling component 990 is proximal opening 944 of the jet fluid channel leading to distal opening of a jet channel (not shown). A jet fluid tube may be inserted through a flexible shaft and may be used for delivering fluid to, and optionally suction of fluid from the body cavity, for cleaning purposes.

On proximal surface 991 of unitary fluid channeling component 990 is proximal opening 965 of the working channel 262 leading to a distal opening of the working channel (not shown).

Unitary fluid channeling component 990 includes groove 950 extending from proximal surface 991 along the length of proximal fluid channeling component section 990'. Groove 950 is adapted to guide (and optionally hold in place) an electric cable(s) which may be connected at its distal end to the electronic components such as cameras and/or light sources in the endoscope's tip section and deliver electrical power and/or command signals to the tip section and/or transmitting video signal from the cameras to be displayed to the user. According to this embodiment the electrical cable(s) do not have to be threaded through proximal fluid channeling component section 990' (which may be complicated) but can be simply placed in groove 950 and held by it.

On proximal surface 991 of unitary fluid channeling component 990 are I/I tubes proximal openings: front I/I proximal opening 910; right side I/I proximal opening; 911 and left side I/I proximal opening 913. Front I/I proximal opening 910; right side I/I proximal opening 911 (not shown) and left side I/I proximal opening 913 lead to front I/I channel 970; right side I/I channel 971 (not shown); and left side I/I channel 973, respectively. Front I/I channel 970 extends from front I/I proximal opening 910, through proximal fluid channeling component section 990' and distal fluid channeling component section 990" to front I/I opening 960. Left side I/I channel 973 extends from right I/I proximal opening 913, through proximal fluid channeling component section 990' to left I/I opening 963. Right side I/I channel 971 (not shown) extends from right I/I proximal opening 911 (not shown), through proximal fluid channeling component section 990' to right I/I opening (not shown), similar to the left side arrangement.

Front I/I channel 970 may include two parts: a proximal part 970' (extending through proximal fluid channeling component section 990') and a distal part 970" extending through distal fluid channeling component section 990"). Proximal part 970' of front I/I channel 970 is adapted to receive, through front I/I proximal opening 910, tube 980 (shown in FIG. 9c) which is adapted to transfer fluid (liquid and/or gas) to front I/I channel 970. Tube 980 may be divided at any point along its length (for example at junction 981) into two tubes, one is adapted to transfer gas and the other is adapted to transfer liquid (such as water).

Left side I/I channel 973 may be adapted to receive, at its proximal part, through left side I/I proximal opening 913, tube 982 (shown in FIG. 9c) which is adapted to transfer fluid (liquid and/or gas) to left side I/I channel 973. Tube 982 may be divided at any point along its length (for example at junction 983) into two tubes, one is adapted to transfer gas and the other is adapted to transfer liquid (such as water).

Right side I/I channel (not shown) may be adapted to receive, at its proximal, through right side I/I proximal opening 911, part tube 984 (shown in FIG. 9c) which is adapted to transfer fluid (liquid and/or gas) to right side I/I channel. Tube 984 may be divided at any point along its length (for example at junction 985) into two tubes, one is adapted to transfer gas and the other is adapted to transfer liquid (such as water).

The endoscope user can thus decide which fluid (gas, liquid or both) he or she would like to pass through the I/I channel, which fluid, as mentioned herein, may be used for cleaning and/or insufflation purposes.

Figure 9C:
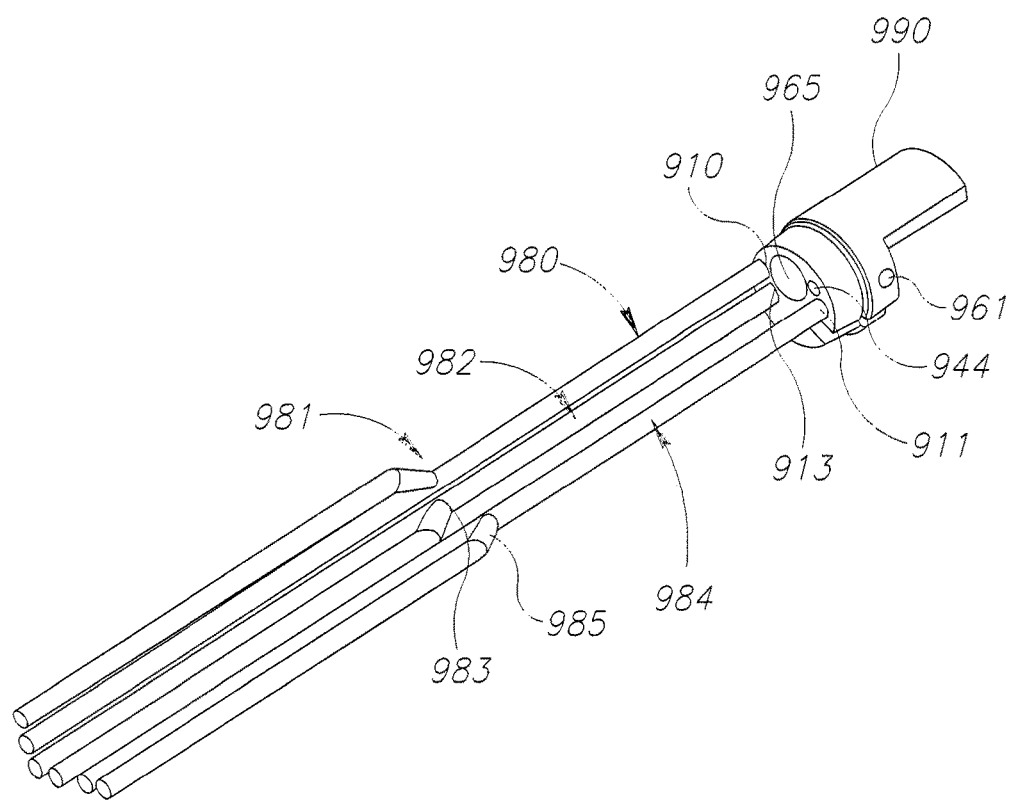
FIG. 9c schematically depicts an isometric proximal view of the main section of FIG. 9a, having liquid and gas tubes connected thereto, according to an exemplary embodiment of the current invention.

FIG. 9c schematically depicts an isometric proximal view of the main section of FIG. 9a, having liquid and gas tubes connected thereto, according to an exemplary embodiment of the current invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What we claim is:

1. A tip section of a multi-camera endoscope, the tip section comprising:
a unitary fluid channeling component adapted to channel fluid, said unitary fluid channeling component comprising:
a proximal section having a proximally-facing surface, a side surface extending distally from the proximal-facing surface, and a cylindrical shape;
a distal section having a partial cylindrical shape, wherein said distal section is integrally formed as a unitary block of material with the proximal section, and wherein the distal section has a distal-facing surface;
a proximal opening located on the proximal-facing surface of the proximal section, said proximal opening being in fluid flow connection with a first fluid channel, wherein the first fluid channel is a passage extending through the unitary block of material from the proximal section, through the distal section, and to a distal opening in said distal-facing surface;
a second fluid channel, wherein said second fluid channel is a passage extending through the unitary block of material and leading to a side opening on the side surface; and
a working channel, wherein the working channel is a passage extending through the unitary block of material from the proximal section, through the distal section, and to a distal opening in the distal-facing surface.

2. The tip section according to claim 1, wherein the side opening is on a first side of the side surface, and wherein the unitary fluid channeling component further comprises a third fluid channel, wherein said third fluid channel is a passage extending through the unitary block of material and leading to a side opening on a second side of the side surface opposite the first side.

3. The tip section according to claim 1, wherein at least a portion of said second fluid channel extends transverse to a longitudinal axis of said unitary fluid channeling component.

4. The tip section according to claim 1, wherein the proximal opening is a first proximal opening and the distal opening is a first distal opening, and wherein said unitary fluid channeling component further comprises a second proximal opening located on the proximal-facing surface of the proximal section, said second proximal opening being in fluid flow connection with third fluid channel, wherein the third fluid channel is a passage extending through the unitary block of material from the proximal section, through the distal section, and to a second distal opening in said distally-facing surface.

5. The tip section according to claim 1, wherein said unitary fluid channeling component further comprises a groove formed in the side surface for guiding a cable.

6. The tip according to claim 1, wherein the unitary block of material is made entirely of metal.

7. A tip section of an endoscope, the tip section comprising:
a fluid channeling component, comprising:
a proximal section having a proximal-facing surface, a distal-facing surface, a side surface extending between the proximal-facing and distal-facing surfaces, and a cylindrical shape;
a distal section having a partial cylindrical shape, wherein said distal section extends distally from the distal-facing surface, wherein the distal section has a distalmost end, and wherein a first distance between the proximal-facing surface and the distal-facing surface is less than a second distance between the distal-facing surface and the distalmost end;
a fluid opening on the proximal-facing surface, said fluid opening being in fluid flow connection with a fluid channel, wherein the fluid channel is a passage extending distally from the fluid opening; and
a working channel opening on the proximal-facing surface, said working channel opening being in communication with a working channel, wherein the working channel is a passage extending distally from the working channel opening.

8. The tip section according to claim 7, wherein the working channel opening is larger than fluid opening.

9. The tip section according to claim 8, wherein the working channel passage terminates at a distal opening at the distalmost end.

10. The tip section according to claim 9, wherein the fluid channel passage terminates at a distal opening at the distalmost end.

11. The tip section according to claim 9, wherein the fluid channel passage terminates distally at an opening proximal to the distal-facing surface.

12. The tip section according to claim 7, wherein the proximal-facing surface is planar.

13. The tip section according to claim 7, wherein the fluid channel has a proximal section and a distal section, and wherein a central longitudinal axis of the proximal section is transverse to a central longitudinal axis of the distal section.

14. A tip section of an endoscope, the tip section comprising:
a fluid channeling component, comprising:
a proximal section having a proximal-facing surface, a distal-facing surface, a side surface extending between the proximal-facing and distal-facing surfaces, and a cylindrical shape;
a distal section having a partial cylindrical shape, wherein said distal section extends distally from the distal-facing surface, wherein the distal section has a distalmost end;
a longitudinally extending groove formed in the side surface;
a plurality of openings on the proximal-facing surface, the plurality of openings including:
a fluid opening, said fluid opening being in fluid flow connection with a fluid channel, wherein the fluid channel is a passage extending distally from the fluid opening; and
a working channel opening, said working channel opening being in communication with a working channel, wherein the working channel is a passage extending distally from the working channel opening.

15. The tip according to claim 14, wherein the fluid channeling component further comprises a proximalmost end, the proximal-facing surface being at the proximalmost end, and wherein the fluid opening is one of a plurality of fluid openings on the proximal-facing surface.

16. The tip according to claim 14, wherein a central longitudinal axis of a proximal portion of the fluid channel extends transverse and non-perpendicular to the proximal-facing surface.

17. The tip according to claim 14, wherein the fluid channel has a proximal portion and a distal portion, the proximal portion having a central longitudinal axis parallel to a central longitudinal axis of the fluid channeling component, and the distal portion having a central longitudinal axis transverse to the central longitudinal axis of the proximal portion.

18. The tip according to claim 14, wherein the fluid channel terminates at an opening in the side surface.

19. The tip according to claim 14, wherein a length of the distal section is greater than a length of the proximal section, and wherein the groove extends the full length of the proximal section.

20. The tip according to claim 14, wherein an entirety of the fluid channeling component is made of metal.

* * * * *